United States Patent
Kinsho et al.

(10) Patent No.: US 9,261,783 B2
(45) Date of Patent: Feb. 16, 2016

(54) FLUORINATED ESTER MONOMER, MAKING METHOD, FLUORINATED ESTER POLYMER, AND DIFLUOROHYDROXYCARBOXYLIC ACID

(71) Applicant: SHIN-ETSU CHEMICAL CO., LTD., Chiyoda-ku, Tokyo (JP)

(72) Inventors: Takeshi Kinsho, Joetsu (JP); Yuuki Suka, Joetsu (JP); Yuji Harada, Joetsu (JP); Koji Hasegawa, Joetsu (JP); Takeshi Sasami, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 118 days.

(21) Appl. No.: 14/060,971

(22) Filed: Oct. 23, 2013

(65) Prior Publication Data
US 2014/0051024 A1    Feb. 20, 2014

Related U.S. Application Data

(62) Division of application No. 13/240,925, filed on Sep. 22, 2011, now Pat. No. 8,697,903.

(30) Foreign Application Priority Data

Oct. 5, 2010    (JP) .................. 2010-225358

(51) Int. Cl.
| | | |
|---|---|---|
| *C08F 222/18* | (2006.01) | |
| *G03F 7/038* | (2006.01) | |
| *C07C 51/00* | (2006.01) | |
| *C07C 69/73* | (2006.01) | |
| *C08F 220/22* | (2006.01) | |
| *G03F 7/027* | (2006.01) | |
| *C08F 220/28* | (2006.01) | |

(52) U.S. Cl.
CPC ............. *G03F 7/038* (2013.01); *C07C 51/00* (2013.01); *C07C 69/73* (2013.01); *C08F 220/22* (2013.01); *C08F 222/18* (2013.01); *G03F 7/027* (2013.01); *C08F 2220/283* (2013.01)

(58) Field of Classification Search
CPC .............................. C08F 220/22; C08F 222/18
See application file for complete search history.

(56) References Cited

U.S. PATENT DOCUMENTS

| | | | | |
|---|---|---|---|---|
| 6,579,658 B2 * | 6/2003 | Hatakeyama et al. | ..... | 430/270.1 |
| 6,607,868 B2 * | 8/2003 | Choi | .......... | 430/270.1 |
| 7,276,623 B2 | 10/2007 | Harada et al. | | |
| 7,488,567 B2 | 2/2009 | Harada et al. | | |
| 7,531,287 B2 | 5/2009 | Kanda et al. | | |
| 7,531,289 B2 | 5/2009 | Kinsho et al. | | |
| 7,537,880 B2 | 5/2009 | Harada et al. | | |
| 7,846,637 B2 | 12/2010 | Ishizuka et al. | | |
| 7,887,990 B2 | 2/2011 | Isono et al. | | |
| 8,420,292 B2 | 4/2013 | Harada et al. | | |
| 2003/0207202 A1 * | 11/2003 | Fujita et al. | ............. | 430/270.1 |
| 2006/0111550 A1 * | 5/2006 | Hata et al. | ..................... | 528/501 |
| 2008/0227037 A1 * | 9/2008 | Hatakeyama et al. | ........ | 430/323 |
| 2008/0311507 A1 | 12/2008 | Isono et al. | | |

(Continued)

FOREIGN PATENT DOCUMENTS

| | | |
|---|---|---|
| JP | 2005-264131 A | 9/2005 |
| JP | 2006-48029 A | 2/2006 |

(Continued)

OTHER PUBLICATIONS

Olivella et al., "New Selective Haloform-type Reaction Yielding 3-Hydroxy-2,2-difluoracids: Theoretical Study of the Mechanism", J.Am. Chem. Soc., vol. 127, No. 8, 2005, (Published online Feb. 4, 2005), pp. 2620-2627.

(Continued)

*Primary Examiner* — Nicole M Buie-Hatcher

(74) *Attorney, Agent, or Firm* — Birch, Stewart, Kolasch & Birch, LLP

(57) ABSTRACT

A fluorinated ester monomer is provided having formula (1) wherein $R^1$ is H, $CH_3$ or $CF_3$, $R^2$ and $R^3$ are H or a monovalent hydrocarbon group, or $R^2$ and $R^3$ forms a hydrocarbon ring, $R^4$ is a monovalent hydrocarbon group, and k is 0 or 1. A polymer obtained from the monomer has transparency to radiation with a wavelength of up to 200 nm and appropriate alkaline hydrolysis, is constructed such that any of water repellency, water slip and surface segregation may be adjusted by a choice of its structure, and is useful in forming ArF immersion lithography materials.

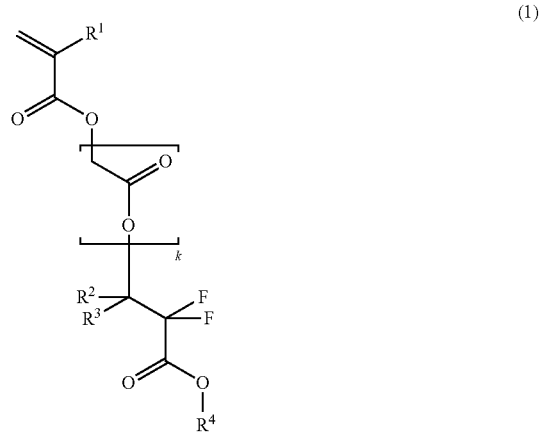

(1)

4 Claims, No Drawings

(56) References Cited

U.S. PATENT DOCUMENTS

| | | | |
|---|---|---|---|
| 2010/0266957 A1* | 10/2010 | Harada et al. | 430/285.1 |
| 2011/0098500 A1 | 4/2011 | Isono et al. | |
| 2011/0104611 A1 | 5/2011 | Sakakibara et al. | |
| 2011/0117491 A1 | 5/2011 | Utsumi et al. | |
| 2011/0151378 A1 | 6/2011 | Matsumura et al. | |
| 2011/0151381 A1 | 6/2011 | Hasegawa et al. | |
| 2011/0212401 A1 | 9/2011 | Nishimura et al. | |

FOREIGN PATENT DOCUMENTS

| | | |
|---|---|---|
| JP | 2006-152255 A | 6/2006 |
| JP | 2008-111103 A | 5/2008 |
| JP | 2009-19199 A | 1/2009 |
| JP | 2010-204187 A | 9/2010 |
| JP | 2011-168691 A | 9/2011 |
| KR | 10-2008-0109621 A | 12/2008 |
| WO | WO 2009/142182 A1 | 11/2009 |

OTHER PUBLICATIONS

Hirayama, "Resist and Cover Material Investigation for Immersion Lithography", 2nd Immersion Workshop, Jul. 11, 2003, 16 pages.

Lin, "Semiconductor Foundry, Lithography, and Partners", Proc. of SPIE, vol. 4690, 2002, pp. xxix-xlii.

Owa et al., "Immersion lithography; its potential performance and issues", Proc. of SPIE, vol. 5040, 2003, pp. 724-733.

\* cited by examiner

US 9,261,783 B2

FLUORINATED ESTER MONOMER, MAKING METHOD, FLUORINATED ESTER POLYMER, AND DIFLUOROHYDROXYCARBOXYLIC ACID

CROSS-REFERENCE TO RELATED APPLICATION

The present application is a 37 C.F.R. §1.53(b) divisional of, and claims priority to, U.S. application Ser. No. 13/240,925, filed Sep. 22, 2011. Priority is also claimed to Japanese Patent Application No. 2010-225358 filed on Oct. 5, 2010. The entire contents of each of these applications is hereby incorporated by reference.

TECHNICAL FIELD

This invention relates to a novel monomer of fluorinated ester structure. The monomer is useful as raw material for the preparation of opto-functional materials and coating materials because a polymer obtained from the monomer has transparency to radiation in a broad wavelength range from visible light to less than 200 nm and appropriate alkaline hydrolysis. The polymer permits any of water repellency, water slip and surface segregation to be adjusted by a choice of its structure and is useful as a photoresist additive or protective film material in preparing ArF immersion lithography materials.

BACKGROUND ART

In the recent drive for higher integration densities and operating speeds in LSI devices, the pattern rule is made drastically finer. The background supporting such a rapid advance is a reduced wavelength of the light source for exposure. The change-over from i-line (365 nm) of a mercury lamp to shorter wavelength KrF excimer laser (248 nm) enabled mass-scale production of dynamic random access memories (DRAM) with an integration degree of 64 MB (processing feature size ≤0.25 µm). To establish the micropatterning technology necessary for the fabrication of DRAM with an integration degree of 256 MB and 1 GB or more, the lithography using ArF excimer laser (193 nm) is under active investigation. The ArF excimer laser lithography, combined with a high NA lens (NA≥0.9), enables mass-scale fabrication of 65-nm node devices. For the fabrication of next 45-nm node devices, the $F_2$ laser lithography of 157 nm wavelength became a candidate. However, because of many problems including a cost and a shortage of resist performance, the employment of $F_2$ lithography was postponed. ArF immersion lithography was proposed as a substitute for the $F_2$ lithography (see Proc. SPIE Vol. 4690, xxix, 2002). Development works are currently concentrated thereon.

In the ArF immersion lithography, the space between the projection lens and the wafer is filled with water and ArF excimer laser is irradiated through the water. Since water has a refractive index of 1.44 at 193 nm, pattern formation is possible even using a lens with NA of 1.0 or greater. The theoretically possible maximum NA is 1.44. The resolution is improved by an increment of NA. A combination of a lens having NA of at least 1.2 with strong super-resolution technology suggests a way to the 45-nm node (see Proc. SPIE Vol. 5040, p 724, 2003).

The ArF immersion lithography wherein exposure is made in the presence of water on a resist film has a possibility that an acid generated in the resist film and a basic compound previously added to the resist material can be, in part, leached in immersion water. As a result, pattern profile changes and pattern collapse can occur. It is also pointed out that water droplets remaining on the resist film after scanning, though in a minute volume, can penetrate into the resist film to generate defects. It was then proposed to provide a protective coating between the resist film and water to overcome these drawbacks (see 2nd Immersion Workshop Resist and Cover Material Investigation for Immersion Lithography, 2003).

Among fluorinated protective film materials, protective films made of perfluoroalkyl compounds use fluorocarbons like Freon® as the diluent for controlling a film thickness and as the stripper for stripping off the protective film after exposure. As is well known, the use of fluorocarbons is a consideration in view of environmental protection. In addition, special units for coating and stripping of the protective film must be added to the existing system. These factors raise serious problems on practical use.

One proposal for mitigating practical drawbacks of the above protective film is a protective film of the type which is soluble in alkaline developer (JP-A 2005-264131). The alkali-soluble protective film is epoch-making in that it eliminates a need for a stripping step or a special stripping unit because it can be stripped off at the same time as the development of a photoresist film. However, there is still left a room for improvement at a practical level because the solvent capable of dissolving the photoresist cannot be selected as the solvent for diluting the protective film material for coating, and a special unit for coating the protective film is necessary.

JP-A 2006-048029 discloses the addition of a hydrophobic fluorinated compound to resist material as the means for inhibiting water from penetrating into a resist film. This method is advantageous over the use of a resist protective film because the steps of forming and removing the protective film are unnecessary. However, when a hydrophobic fluorinated compound is added to a resist material, the resulting resist film on its surface has an increased contact angle, especially after development, tending to form defects known as "blob defects." It is then desired to have a resist additive which serves to reduce the contact angle of a resist film as developed while maintaining effective water barrier properties and for further performance improvements, to have a novel monomer that reflects such a design concept and whose structure can be tailored so as to comply with any particular performance required.

CITATION LIST

Patent Document 1: JP-A 2005-264131
Patent Document 2: JP-A 2006-048029
Patent Document 3: JP-A 2006-152255
Non-Patent Document 1: Proc. SPIE Vol. 4690 xxix (2002)
Non-Patent Document 2: Proc. SPIE Vol. 5040, p 724 (2003)
Non-Patent Document 3: 2nd Immersion Workshop, Resist and Cover Material Investigation for Immersion Lithography (2003)

DISCLOSURE OF THE INVENTION

An object of the present invention is to provide a novel monomer which is useful not only as a raw material for the preparation of opto-functional materials, coating materials or the like, but also for the preparation of a polymer to be formulated in resist compositions. The polymer obtained from the monomer has transparency to radiation having a wavelength of up to 200 nm and appropriate alkaline hydrolysis, permits any of water repellency, water slip and surface segregation to be adjusted by a choice of its structure, and is thus useful as a photoresist additive or protective film material in forming ArF immersion lithography materials. Another object is to provide a method for preparing the monomer from a reactant which is readily available and easy to handle, a polymer obtained from the monomer, and an intermediate useful in the method.

The inventors have found that a fluorinated ester monomer having the general formula (1) shown below can be readily prepared in high yields, and that a polymer resulting from polymerization of the monomer has adequate alkaline hydrolysis and permits any one of desired properties be adjusted by a choice of its structure.

Accordingly, the present invention provides a fluorinated ester monomer, making method, fluorinated ester polymer, and difluorohydroxycarboxylic acid, as defined below.

In a first aspect, the invention provides a fluorinated ester monomer having the general formula (1):

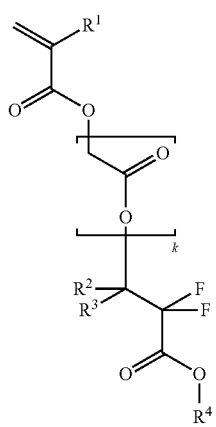

(1)

wherein $R^1$ is hydrogen, methyl or trifluoromethyl, $R^2$ and $R^3$ are each independently hydrogen or a straight, branched or cyclic monovalent $C_1$-$C_{20}$ hydrocarbon group, or $R^2$ and $R^3$ taken together represent a divalent group which forms a $C_3$-$C_{20}$ hydrocarbon ring with the carbon atom to which they are attached, $R^4$ is a straight, branched or cyclic, primary or secondary, monovalent hydrocarbon group of 1 to 20 carbon atoms in which a hydrogen atom may be replaced by a fluorine atom or in which a methylene moiety may be replaced by an oxygen atom or carbonyl radical, and k is 0 or 1.

In preferred embodiments, $R^4$ is a primary $C_1$-$C_5$ alkyl group; $R^4$ is a $C_2$-$C_8$ fluoroalkyl group; $R^4$ is an alkyloxyalkyl group: MeO(CH$_2$CH$_2$O)$_n$CH$_2$CH$_2$— or EtO(CH$_2$CH$_2$O)$_n$CH$_2$CH$_2$— wherein Me is methyl, Et is ethyl, and n is 0, 1 or 2; or $R^4$ is a group having the general formula (A):

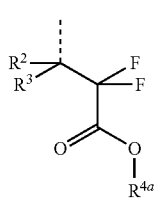

(A)

wherein $R^2$ and $R^3$ are as defined above, $R^{4a}$ is a primary $C_1$-$C_5$ alkyl group, a $C_2$-$C_8$ fluoroalkyl group or a group: MeO(CH$_2$CH$_2$O)$_n$CH$_2$CH$_2$— or EtO(CH$_2$CH$_2$O)$_n$CH$_2$CH$_2$— wherein Me is methyl, Et is ethyl, and n is 0, 1 or 2, and the broken line denotes a valence bond.

In a second aspect, the invention provides a polymer comprising recurring units having the general formula (1a):

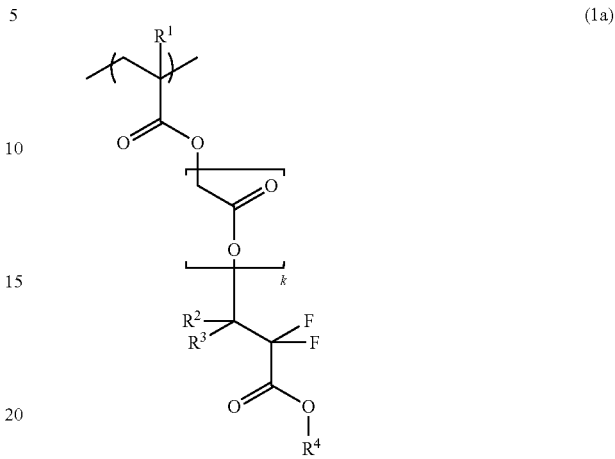

(1a)

wherein $R^1$, $R^2$, $R^3$, $R^4$, and k are as defined above.

In a third aspect, the invention provides a difluorohydroxycarboxylic acid compound having the general formula (3), obtained by treating a pentafluorohydroxyketone compound having the general formula (2) with a base,

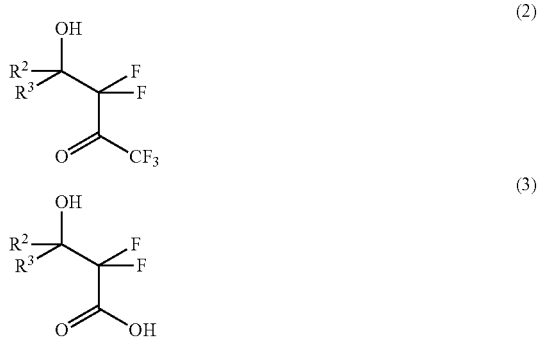

wherein $R^2$ and $R^3$ are as defined above.

In a fourth aspect, the invention provides a method for preparing the fluorinated ester monomer defined above, comprising the steps of esterifying a carboxyl group of a difluorohydroxy carboxylic acid compound having the general formula (3) to form a difluorohydroxy ester compound, and acylating a hydroxyl group of the difluorohydroxy ester compound.

Advantageous Effects of Invention

The fluorinated ester monomer is useful as a raw material for the preparation of opto-functional materials, coating materials or the like. The polymer obtained from the monomer has high transparency to radiation having a wavelength of up to 200 nm and appropriate alkaline hydrolysis. The polymer permits any of desired properties including water repellency, water slip and surface segregation to be adjusted by a choice of its structure. The polymer is thus useful as a photoresist additive or protective film material in forming ArF immersion lithography materials. The intermediate is useful in the course of synthesis of the monomer.

DESCRIPTION OF THE PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. As used herein, the terminology "$(C_x-C_y)$", as applied to a particular unit, such as, for example, a chemical compound or a chemical substituent group, means having a carbon atom content of from "x" carbon atoms to "y" carbon atoms per such unit.

The abbreviations and acronyms have the following meaning.

Mw: weight average molecular weight
Mn: number average molecular weight
GPC: gel permeation chromatography
PEB: post-exposure baking
PAG: photoacid generator A first embodiment of the invention is a fluorinated ester monomer having the general formula (1).

(1)

Herein $R^1$ is hydrogen, methyl or trifluoromethyl. $R^2$ and $R^3$ are each independently hydrogen or a straight, branched or cyclic monovalent $C_1-C_{20}$ hydrocarbon group, or $R^2$ and $R^3$ taken together represent a divalent group which forms a $C_3-C_{20}$ hydrocarbon ring with the carbon atom to which they are attached. $R^4$ is a straight, branched or cyclic, primary or secondary, monovalent hydrocarbon group of 1 to 20 carbon atoms in which one or more hydrogen atom may be replaced by a fluorine atom or in which one or more methylene moiety may be replaced by an oxygen atom or carbonyl radical, and k is 0 or 1.

In formula (1), $R^2$ and $R^3$ may be straight, branched or cyclic monovalent $C_1-C_{20}$ hydrocarbon groups. Exemplary monovalent hydrocarbon groups are straight, branched or cyclic alkyl groups and aryl groups including methyl, ethyl, propyl, isopropyl, n-butyl, isobutyl, sec-butyl, tert-butyl, n-pentyl, isopentyl, tert-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, methyltetracyclo[4.4.0.1$^{2,5}$.1$^{7,10}$]dodecylmethyl, ethyltetracyclo[4.4.0.1$^{2,5}$.1$^{7,10}$]dodecylmethyl, ethyltetracyclo[4.4.0.1$^{2,5}$.1$^{7,10}$]dodecylethyl, phenyl, tolyl, and naphthyl. Since the foregoing groups may contain aliphatic unsaturation, alkenyl and alkynyl groups are also included.

$R^2$ and $R^3$ may bond together to form a $C_3-C_{20}$ hydrocarbon ring with the carbon atom to which they are attached. Exemplary hydrocarbon rings are $C_3-C_{20}$ alicyclic hydrocarbons including cyclopropane, cyclobutane, cyclopentane, cyclohexane, bicyclo[2.2.1]heptane, bicyclo[2.2.2]octane, tricyclo[5.2.1.0$^{2,6}$]decane, adamantane, and tetracyclo[4.4.0.1$^{2,5}$.1$^{7,10}$]dodecane. Also included are fused rings containing at least one of the foregoing, and substituted forms of the alicyclic hydrocarbons in which some hydrogen atoms are replaced by monovalent hydrocarbon radicals such as straight, branched or cyclic alkyl radicals. The foregoing groups may contain an unsaturated bond.

$R^4$ is a straight, branched or cyclic, primary or secondary, monovalent hydrocarbon group of 1 to 20 carbon atoms in which one or more hydrogen atom may be replaced by a fluorine atom or in which one or more methylene moiety may be replaced by an oxygen atom or carbonyl radical. Examples include methyl, ethyl, propyl, isopropyl, n-butyl, isobutyl, sec-butyl, n-pentyl, isopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, cyclohexylpentyl, cyclohexylhexyl, cyclohexylheptyl, cyclohexyloctyl, cyclohexylnonyl, cyclohexyldecyl, methyl cyclohexylmethyl, ethyl cyclohexylmethyl, ethylcyclohexylethyl, butylcyclohexylbutyl, pentylcyclohexylpentyl, hexylcyclohexylhexyl, heptylcyclohexylheptyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, 8-tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantylmethyl, adamantylethyl, adamantylbutyl, methyladamantylmethyl, ethyladamantylmethyl, ethyladamantylethyl, 3-tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, methyltetracyclo[4.4.0.1$^{2,5}$.1$^{7,10}$]dodecylmethyl, ethyltetracyclo[4.4.0.1$^{2,5}$.1$^{7,10}$]dodecylmethyl, ethyltetracyclo[4.4.0.1$^{2,5}$.1$^{7,10}$]dodecylethyl, trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, 2-(perfluorodecyl)ethyl, 3,3,4,4,5,5,6,6,6-nonafluorohexyl, methoxyethyl, methoxyethoxyethyl, methoxyethoxyethoxyethyl, ethoxyethyl, and ethoxyethoxyethyl.

Preferably, $R^4$ is a primary $C_1$-$C_5$ alkyl group, a $C_2$-$C_5$ fluoroalkyl group, $MeO(CH_2CH_2O)_nCH_2CH_2$— or $EtO(CH_2CH_2O)_nCH_2CH_2$— wherein Me is methyl, Et is ethyl, and n is 0, 1 or 2, or a group having the following general formula (A):

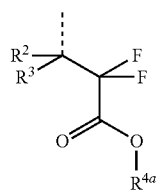

(A)

wherein $R^2$ and $R^3$ are as defined above, $R^{4a}$ is a primary $C_1$-$C_5$ alkyl group, a $C_2$-$C_8$ fluoroalkyl group or a group: $MeO(CH_2CH_2O)_nCH_2CH_2$— or $EtO(CH_2CH_2O)_nCH_2CH_2$— wherein Me is methyl, Et is ethyl, and n is 0, 1 or 2, and the broken line denotes a valence bond.

By a choice of the structure of these substituent groups $R^2$, $R^3$, and $R^4$, a polymer prepared from the monomer can be tailored in various properties including alkaline hydrolysis, water repellency, water slip, and surface segregation. The monomer is characterized by a very high freedom of molecular design. The design concept of the monomer is described below as well as preferred examples of the substituent groups $R^2$, $R^3$, and $R^4$.

Function (1) is water repellency. For the polymer used as a photoresist additive or protective film material in formulating ArF water immersion lithography materials, water repellency is essentially necessary to provide a barrier function of preventing penetration of water. For water repellency, the inclusion of a fluorinated hydrocarbon group (or fluorocarbon, typically fluoroalkyl) is preferred. Function (2) is surface segregation. When a photoresist additive is premixed in a resist material, the additive can be segregated on the surface during resist film formation by utilizing a difference of surface energy so that the additive may function as a protective film. The inclusion of a fluoroalkyl group is one of means for surface segregation. Function (3) is water slip. During exposure, water present between the protective film and the lens should move away smoothly without leaving droplets. Smooth water slip is accomplished by increasing the contact angle with water of the protective film surface, specifically the receding contact angle thereof. To this end, the inclusion of a hydrophobic hydrocarbon group, typically branched alkyl group as well as the fluorocarbon group, typically fluoroalkyl group is preferred. Function (4) is alkaline hydrolysis. It is desired that the protective film be removed at the same time as development of a resist film with a developer, specifically aqueous alkaline solution, and the contact angle with water of the resist film surface after removal of the protective film is kept low for restraining formation of blob and other defects. The present monomer has an ester functional group susceptible to alkaline hydrolysis, which ensures the function that the polymer becomes alkali soluble after hydrolysis. The alkaline hydrolysis is the key function of the present monomer.

Of these functions, a certain function can be assigned to a comonomer to be copolymerized along with the present monomer during manufacture of a polymer so that the polymer as a whole may fulfill the necessary functions. The comonomer to be used in copolymerization will be described later.

As to the site where a fluoroalkyl group is introduced for water repellency and water slip, a choice of $R^2$ or $R^3$ is acceptable. However, when the preparation method to be described later is employed, it is preferred to introduce a fluoroalkyl group into $R^4$ because a starting reactant is readily available and inexpensive.

A second embodiment of the invention is a polymer or high molecular weight compound comprising recurring units having the general formula (1a).

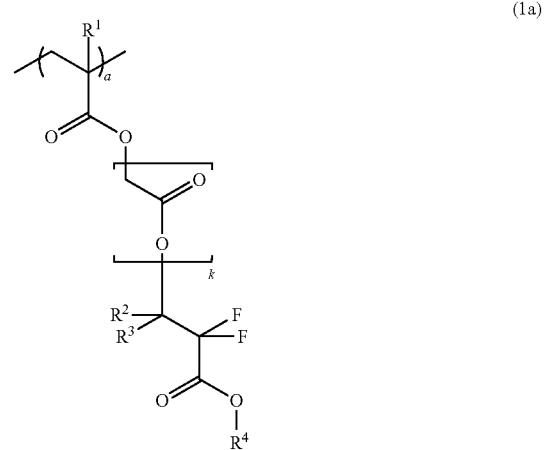

(1a)

Herein $R^1$ is hydrogen, methyl or trifluoromethyl, $R^2$ and $R^3$ are each independently hydrogen or a straight, branched or cyclic monovalent $C_1$-$C_{20}$ hydrocarbon group, or $R^2$ and $R^3$ taken together represent a divalent group which forms a $C_3$-$C_{20}$ hydrocarbon ring with the carbon atom to which they are attached, $R^4$ is a straight, branched or cyclic, primary or secondary, monovalent hydrocarbon group of 1 to 20 carbon atoms in which one or more hydrogen atom may be replaced by a fluorine atom or in which one or more methylene moiety may be replaced by an oxygen atom or carbonyl radical, k is 0 or 1, and "a" is a number in the range: $0<a\leq1.0$.

First described is the fluorinated polymer having formula (1a) wherein k=0. The polymer is susceptible to hydrolysis at two sites in the molecule, as depicted in the following reaction schemes A and B. The polymer solubilizing function is exerted independent of whether hydrolysis takes place at either one site or both sites.

Scheme A

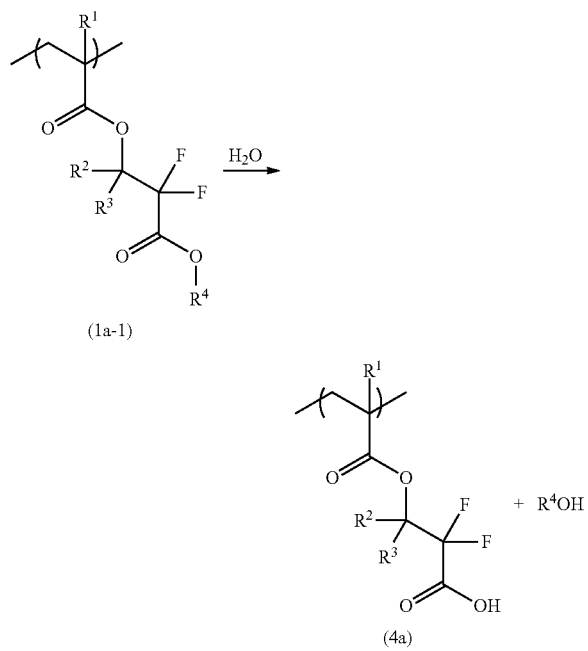

Scheme B

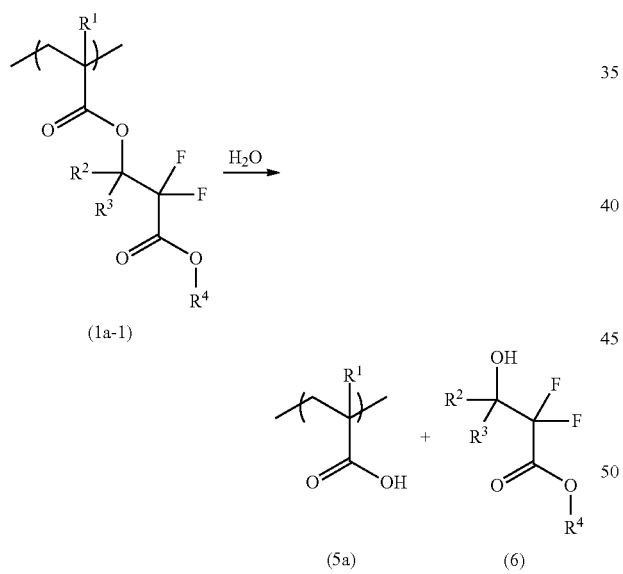

Scheme C

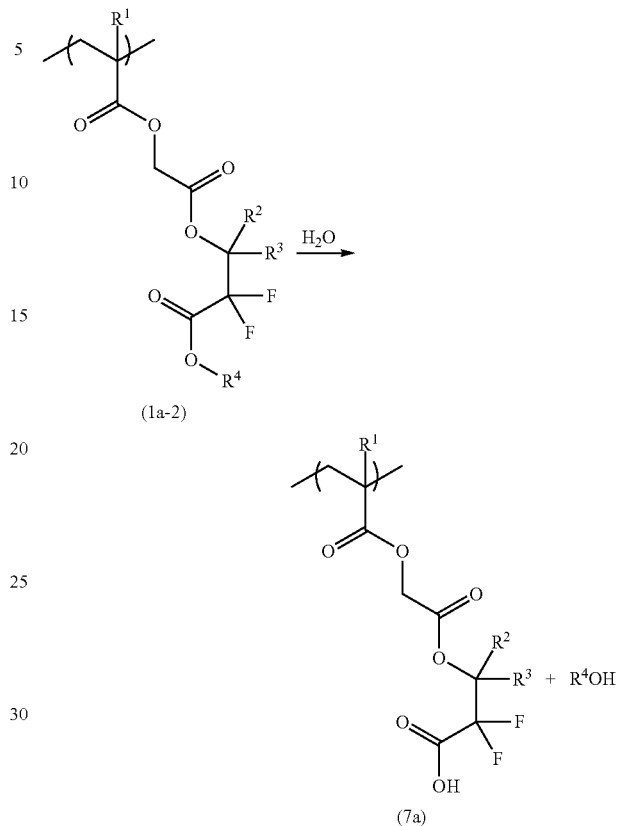

Scheme D

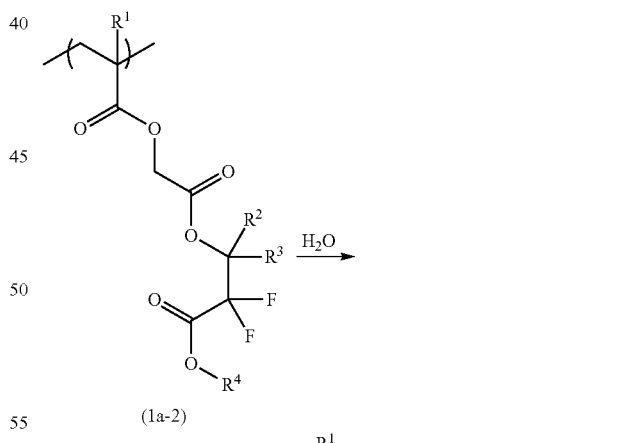

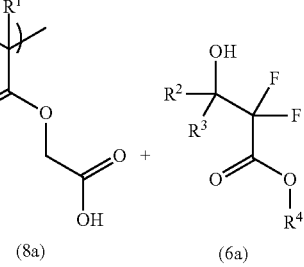

The difluorocarboxylic acid formed in Scheme A is strongly acidic and highly alkali soluble. In particular, the polymer is more susceptible to hydrolysis according to Scheme A when a short-chain alkyl, fluoroalkyl or alkyloxy-alkyl group is selected as $R^4$, which embodiment is preferred.

Next described is the fluorinated polymer having formula (1a) wherein k=1. The polymer is susceptible to hydrolysis at three sites in the molecule, as depicted in the following reaction schemes C, D and E. The polymer solubilizing function is exerted independent of whether hydrolysis takes place at any one site, two sites or three sites.

Scheme E

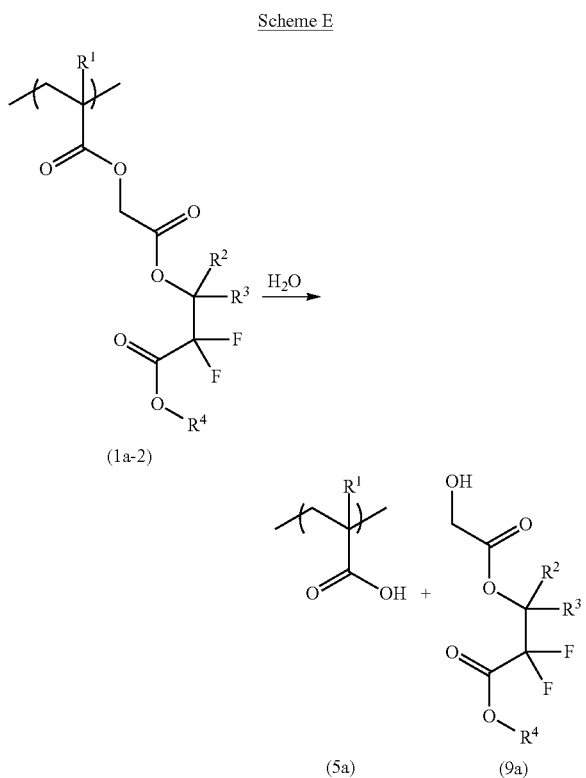

As will be described in Examples, a comparison of fluorinated polymers having formula (1a) wherein k=0 and k=1 reveals that the polymer with k=1 becomes more alkali soluble. Several reasons are presumable. One reason (1) is that the number of hydrolyzable sites increases from two to three. Another reason (2) is that hydrolysis according to Scheme D takes place more readily than hydrolysis according to Scheme B. A further reason (3) is that while hydrolysis sensitivity in Scheme C can be enhanced by the same choice of $R^4$ as described above for Scheme A, hydrolysis sensitivity in Scheme C is more facilitated because the hydrolyzable site is positioned remoter from the polymer backbone.

From the standpoint of hydrolysis under alkaline conditions, $R^4$ is desirably selected from substituent groups which are more susceptible to hydrolysis, for example, a short-chain alkyl group which is susceptible to hydrolysis due to less steric hindrance and relatively high hydrophilicity, a fluoroalkyl group which is susceptible to hydrolysis and is hydrolyzed to form an alcoholic hydroxyl group of higher acidity, and an alkyloxyalkyl group which is susceptible to hydrolysis due to high hydrophilicity and water miscibility.

Examples of the short-chain alkyl group of $R^4$ include methyl, ethyl, n-propyl, n-butyl, isopropyl, and isobutyl. Examples of the fluoroalkyl group of $R^4$ include 2,2,2-trifluoroethyl, 1,1,1,3,3,3-hexafluoroisopropyl, 2,2,3,3,4,4,5,5-octafluoropentyl, and 3,3,4,4,5,5,6,6,6-nonafluorohexyl. Examples of the alkyloxyalkyl group of $R^4$ include methoxyethyl, methoxyethoxyethyl, methoxyethoxyethoxyethyl, ethoxyethyl, and ethoxyethoxyethyl.

Examples of $R^{4a}$ include methyl, ethyl, n-propyl, n-butyl, isopropyl, isobutyl, 2,2,2-trifluoroethyl, 1,1,1,3,3,3-hexafluoroisopropyl, 2,2,3,3,4,4,5,5-octafluoropentyl, 3,3,4,4,5,5,6,6,6-nonafluorohexyl, methoxyethyl, methoxyethoxyethyl, methoxyethoxyethoxyethyl, ethoxyethyl, and ethoxyethoxyethyl.

The present monomer serves for the center function of alkaline hydrolysis. The function of the present monomer is essentially distinguishable from the monomer, described in JP-A 2009-19199 (U.S. Pat. No. 7,887,990, KR 20080109621), in which a portion corresponding to $R^4$ as defined herein is substituted with an acid labile protective group, i.e., a substituent group (typically tertiary alkyl) which undergoes acid-catalyzed elimination reaction under acidic conditions to form a carboxyl group.

A monovalent hydrocarbon group having hydrophobic property for imparting water slip is preferably introduced into $R^2$ and $R^3$. Examples of the monovalent hydrocarbon group include straight hydrocarbon groups such as methyl, ethyl, n-propyl, n-butyl, n-pentyl, n-hexyl, and n-heptyl, branched hydrocarbon groups such as isopropyl, isobutyl, sec-butyl, 2-pentyl, 3-pentyl, 3-methylbutyl, 2-methylbutyl, 4-methylpentyl, 3-methylpentyl, 2-methylpentyl, 2-hexyl, 3-ethylpentyl, 2-ethylpentyl, and neopentyl, and cyclic hydrocarbon groups such as cyclopentyl and cyclohexyl. These groups may contain an unsaturated bond.

Where both $R^2$ and $R^3$ are hydrocarbon groups, preferably they are each independently selected from $C_1$-$C_4$ alkyl groups such as methyl, ethyl, n-propyl and n-butyl. Where one of $R^2$ and $R^3$ is hydrogen and the other is a hydrocarbon group, the hydrocarbon group is preferably selected from straight alkyl groups of more than 3 carbon atoms such as n-butyl, n-pentyl, n-hexyl and n-heptyl, and branched alkyl groups such as isopropyl, isobutyl, sec-butyl, 2-pentyl, 3-pentyl, 3-methylbutyl, 2-methylbutyl, 4-methylpentyl, 3-methylpentyl, 2-methylpentyl, 2-hexyl, 3-ethylpentyl, 2-ethylpentyl, and neopentyl. Inter alia, a branched alkyl is preferred as $R^2$ or $R^3$ for imparting water slip as will be demonstrated in Examples.

Now it is described how to prepare the fluorinated ester monomer defined herein. The method for preparing a fluorinated ester monomer is not limited thereto.

In connection with synthesis of the fluorinated ester monomer defined herein, it is believed that if a hydroxycarboxylic acid compound having the general formula (3) can be synthesized and used as a synthesis intermediate, then various derivatives having different $R^1$ and $R^4$ can be synthesized from a common intermediate by two esterification reactions. It has been found that when a lithium enolate resulting from 1,1,1,3,3,3-hexafluoro-2-propanol under the action of n-butyllithium is reacted with a carbonyl compound, a pentafluorohydroxyketone compound having formula (2) is synthesized, and that when the pentafluorohydroxyketone compound (2) is treated under basic conditions, haloform reaction-like conversion (or decarbonizing reaction) takes place to produce a difluorohydroxycarboxylic acid compound (3) in high yields. The steps are described in detail.

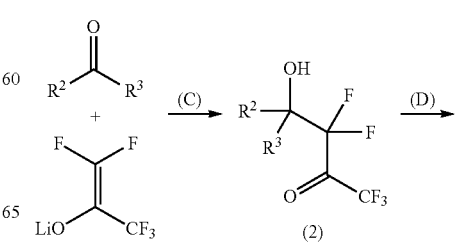

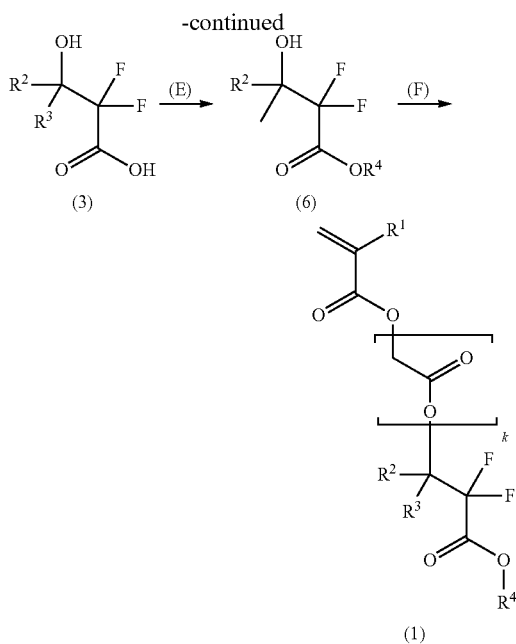

Step C is reaction of a lithium enolate resulting from 1,1,1,3,3,3-hexafluoro-2-propanol under the action of n-butyllithium with a carbonyl compound to form a pentafluorohydroxyketone compound (2). An amount of 1,1,1,3,3,3-hexafluoro-2-propanol used is desirably 0.5 to 2.0 moles, more desirably 1.0 to 1.2 moles per mole of the carbonyl compound. An amount of n-butyllithium used is desirably 1.0 to 2.5 moles, more desirably 1.8 to 2.0 moles per mole of 1,1,1,3,3,3-hexafluoro-2-propanol.

Reaction may be conducted in the absence or presence of a solvent. Examples of the solvent which can be used herein include hydrocarbons such as hexane, heptane, benzene, toluene and xylene, ethers such as diethyl ether, dibutyl ether, tetrahydrofuran, 1,4-dioxane, diglyme, and triglyme, aprotic polar solvents such as N,N-dimethylformamide, N,N-dimethylacetamide, dimethyl sulfoxide, N-methylpyrrolidone, tetramethylethylenediamine, N,N'-dimethylpropyleneurea, 1,3-dimethyl-2-imidazolidinone, and hexamethylphosphoric acid triamide, nitriles such as acetonitrile, and amines such as pyridine and triethylamine. The solvent may be selected and used alone or in admixture, depending on reaction conditions.

The reaction temperature may be selected in the range from −40° C. to the reflux temperature of the solvent, depending on the reaction rate. The reaction time is determined as appropriate by monitoring the reaction process by gas chromatography (GC) or thin-layer chromatography (TLC) because it is desirable from the yield aspect to drive the reaction to completion. Usually the reaction time is about 0.1 to about 20 hours. The desired pentafluorohydroxyketone compound (2) may be recovered from the reaction mixture by ordinary aqueous work-up. If necessary, the compound (2) may be purified by standard techniques like distillation, chromatography, and recrystallization.

Step D is treatment of pentafluorohydroxyketone compound (2) with a NaOH aqueous solution to induce haloform reaction-like conversion to form a difluorohydroxycarboxylic acid compound (3). An amount of NaOH used is desirably 0.5 to 2.0 moles, more desirably 1.0 to 1.2 moles per mole of compound (2). The reaction may be conducted in a solventless system. The reaction temperature may be selected in the range of 0° C. to 100° C., depending on the reaction rate. The reaction time is determined as appropriate by monitoring the reaction process by gas chromatography (GC) or thin-layer chromatography (TLC) because it is desirable from the yield aspect to drive the reaction to completion. Usually the reaction time is about 0.1 to about 20 hours. The desired difluorohydroxycarboxylic acid compound (3) may be recovered from the reaction mixture by ordinary aqueous work-up. If necessary, the compound (3) may be purified by standard techniques like distillation, chromatography, and recrystallization.

Step E is esterification reaction between the difluorohydroxycarboxylic acid compound (3), specifically a carboxyl group thereof and an alcohol compound $R^4OH$ to synthesize a difluorohydroxy ester compound (6). Although the esterification reaction between carboxylic acid compound (3) and alcohol compound $R^4OH$ may be conducted in a solventless system, a solvent may be used in an auxiliary manner. The carboxylic acid compound (3) and alcohol compound $R^4OH$ may be reacted in a solvent such as toluene or hexane by heating the reaction mixture in the presence of an acid catalyst, while water formed during the reaction may be removed out of the system, if desired. Suitable acid catalysts used herein include mineral acids such as hydrochloric acid, sulfuric acid, nitric acid and perchloric acid and organic acids such as p-toluenesulfonic acid and benzenesulfonic acid. An amount of the catalyst used is preferably 0.001 to 5.0 moles, more preferably 0.001 to 0.1 mole per mole of carboxylic acid compound (3). While the reaction temperature varies with other reaction conditions, it is preferably in a range of 50 to 200° C. The reaction time is determined as appropriate by monitoring the reaction process by gas chromatography (GC) or thin-layer chromatography (TLC) because it is desirable from the yield aspect to drive the reaction to completion. Usually the reaction time is about 0.1 to about 20 hours. The desired difluorohydroxy ester compound (6) may be recovered from the reaction mixture by ordinary aqueous work-up. If necessary, the compound (6) may be purified by standard techniques like distillation and chromatography.

Alternatively, the esterification reaction may be conducted by feeding a carboxylic acid and an inorganic halogen compound to a reaction system, thereby forming a carboxylic acid salt compound in situ, and reacting it with an alcohol compound $R^4OH$. Suitable inorganic halogen compounds used herein include phosphoryl chloride, thionyl chloride, phosphorus pentachloride, phosphorus trichloride, and oxalyl chloride. Suitable solvents used herein include benzene and toluene. Although the reaction runs in the absence of a catalyst, a catalyst may be used if desired, for example, zinc chloride, pyridine, iodine or triethylamine. The resulting carboxylic acid chloride is then reacted with an alcohol compound $R^4OH$ in the presence of a base to form the difluorohydroxy ester compound (6). Examples of the base used herein include pyridine, dimethylaniline, tetramethylurea, triethylamine, and metallic magnesium. Suitable solvents include acetonitrile and diethyl ether.

Step F is acylation reaction of difluorohydroxy ester compound (6), specifically a hydroxyl group thereof. In case k=0, difluorohydroxy ester compound (6) is subjected to acryloyl, methacryloyl, or α-trifluoromethylacryloyl-forming reaction into fluorinated ester monomer (1).

The reaction may readily proceed in a well-known manner. Suitable acylating agents include acryloyl chloride, methacryloyl chloride, α-trifluoromethylacryloyl chloride, acrylic acid, methacrylic acid, α-trifluoromethylacrylic acid, acrylic anhydride, methacrylic anhydride, and α-trifluoromethylacrylic anhydride. In the event that the acylating agent is acryloyl chloride, methacryloyl chloride or α-trifluoromethylacryloyl chloride, the difluorohydroxy ester compound, the acylating agent, and a base (e.g., triethylamine, pyridine, or 4-dimethylaminopyridine) are successively or simultaneously added to a solventless system or to a solvent such as methylene chloride, acetonitrile, toluene, or hexane, while the reaction system may be cooled or heated as desired. In the event that the acylating agent is acrylic acid, methacrylic acid or α-trifluoromethylacrylic acid, the difluorohydroxy ester compound and the acylating agent in a solvent such as toluene or hexane are heated in the presence of an acid catalyst, while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid. In the event that the acylating agent is acrylic anhydride, methacrylic anhydride or α-trifluoromethylacrylic anhydride, the difluorohydroxy ester compound, the acylating agent, and a base (e.g., triethylamine, pyridine, or 4-dimethylaminopyridine) are successively or simultaneously added to a solvent such as toluene, while the reaction system may be cooled or heated as desired.

In case k=1, difluorohydroxy ester compound (6) is subjected to acryloyloxyacetyl, methacryloyloxyacetyl, or α-trifluoromethylacryloyloxyacetyl-forming reaction into fluorinated ester monomer (1).

The reaction may readily proceed in a well-known manner. Suitable acylating agents include acryloyloxyacetyl chloride, methacryloyloxyacetyl chloride, α-trifluoromethylacryloyloxyacetyl chloride, acryloyloxyacetic acid, methacryloyloxyacetic acid, and α-trifluoromethylacryloyloxyacetic acid. In the event that the acylating agent is acryloyloxyacetyl chloride, methacryloyloxyacetyl chloride or α-trifluoromethylacryloyloxyacetyl chloride, the difluorohydroxy ester compound (6), the acylating agent, and a base (e.g., triethylamine, pyridine, or 4-dimethylaminopyridine) are successively or simultaneously added to a solventless system or to a solvent such as methylene chloride, acetonitrile, toluene, or hexane, while the reaction system may be cooled or heated as desired. In the event that the acylating agent is acryloyloxyacetic acid, methacryloyloxyacetic acid or α-trifluoromethylacryloyloxyacetic acid, the difluorohydroxy ester compound (6) and the acylating agent in a solvent such as toluene or hexane are heated in the presence of an acid catalyst, while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid.

The above-described synthesis process is versatile and very useful because the difluorohydroxycarboxylic acid compound (3) can be readily prepared by starting with 1,1,1,3,3,3-hexafluoro-2-propanol and a carbonyl compound which are readily available from suppliers, and a variety of fluorinated monomers (1) can be synthesized therefrom by esterification of carboxyl group and acylation of hydroxyl group. By contrast, the preparation process relying on the Reformatsky reaction using a bromodifluoroacetic acid ester compound, described in JP-A 2009-019199, is substantially limited in versatility because the portion corresponding to $R^4$ defined herein is already contained in the reagent used, halodifluoroacetic acid ester compound. For the synthesis of a variety of monomers, a corresponding halodifluoroacetic acid ester compound must be individually prepared.

The present polymer may be either a homopolymer of the present monomer or a copolymer of the present monomer with another monomer or monomers. Preferred recurring units derived from the other monomer are those of the following formula (i) or (ii):

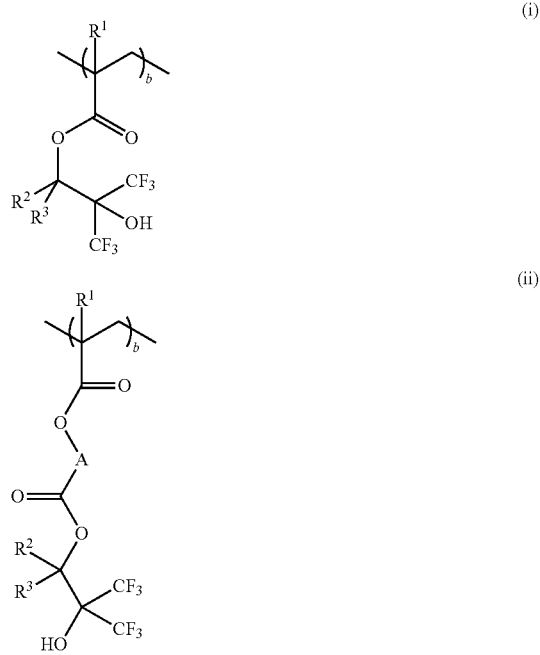

wherein $R^1$, $R^2$, and $R^3$ are as defined above, A is a divalent hydrocarbon group, typically a straight, branched or cyclic $C_1$-$C_6$ alkylene group, and b is a number in the range: $0 \leq b < 1.0$.

Preferably the polymer comprises recurring units of formula (1a) and recurring units of formula (i) or (ii). Their proportion is in the range: $0 < a \leq 1.0$ and $0 \leq b < 1.0$. Better results are obtained from the range: $0 < a \leq 0.8$ and $0 \leq b \leq 0.9$, and more preferably $0 < a \leq 0.6$ and $0 \leq b \leq 0.8$. The sum of a and b is preferably $0.1 \leq a+b \leq 1.0$, and more preferably $0.3 \leq a+b \leq 1.0$. In the case of $a+b < 1.0$, other recurring units may include recurring units of at least one type selected from the following general formulae (10a) to (10i).

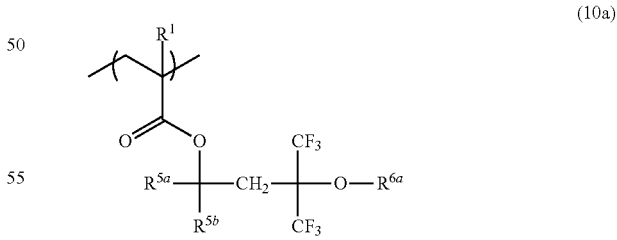

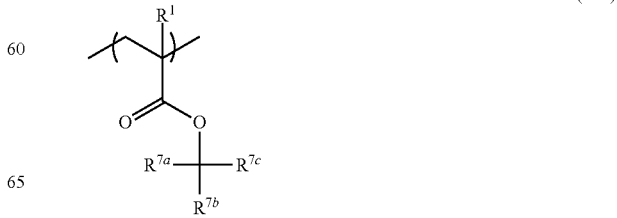

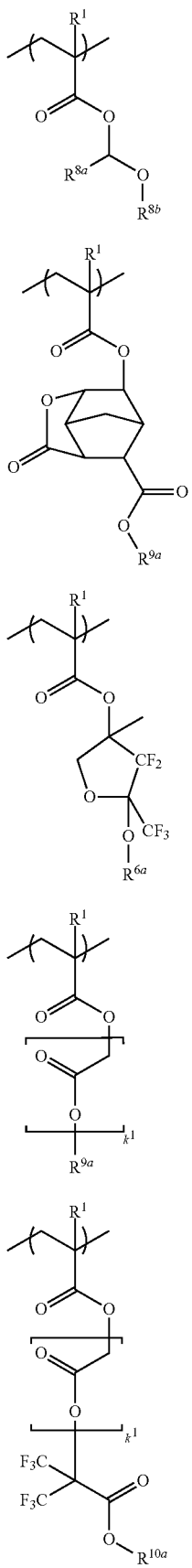
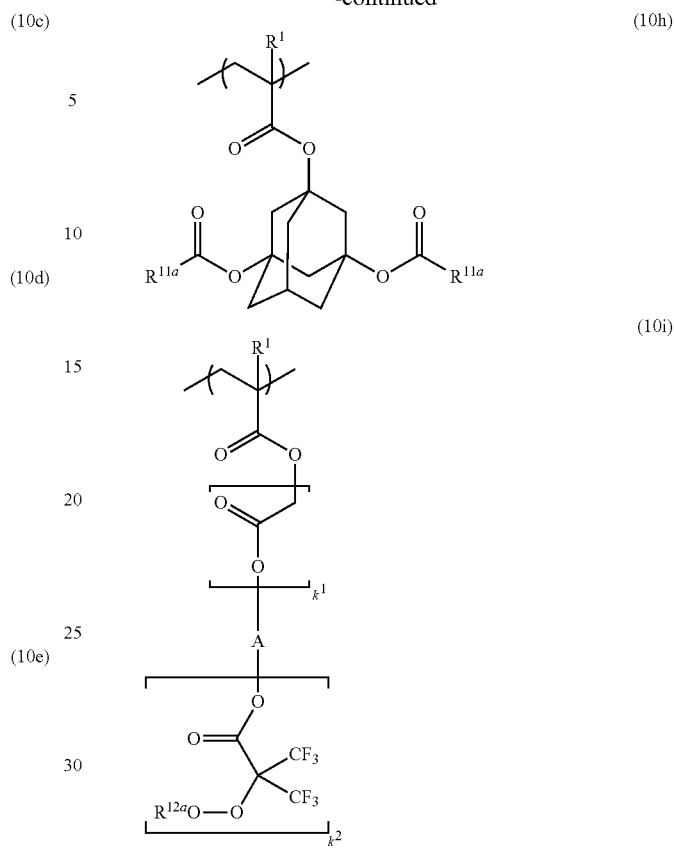

Herein $R^1$ is as defined above. $R^{5a}$ and $R^{5b}$ are hydrogen or a straight, branched or cyclic, $C_1$-$C_{15}$ monovalent hydrocarbon group, and $R^{5a}$ and $R^{5b}$ may bond together to form a $C_3$-$C_8$ non-aromatic ring with the carbon atom to which they are attached. $R^{6a}$ is hydrogen, a straight, branched or cyclic, $C_1$-$C_{15}$ monovalent hydrocarbon or fluorinated hydrocarbon group in which any constituent moiety —$CH_2$— may be replaced by —O— or —C(=O)—, or an acid labile group. $R^{7a}$, $R^{7b}$, and $R^{7c}$ are hydrogen, or a straight, branched or cyclic, $C_1$-$C_{15}$ monovalent hydrocarbon group, and a pair of $R^{7a}$ and $R^{7b}$, $R^{7a}$ and $R^{7c}$, and $R^{7b}$ and $R^{7c}$ may bond together to form a $C_3$-$C_8$ non-aromatic ring with the carbon atom to which they are attached. $R^{8a}$ is hydrogen or a straight, branched or cyclic, $C_1$-$C_{15}$ monovalent hydrocarbon group, $R^{8b}$ is a straight, branched or cyclic, $C_1$-$C_{15}$ monovalent hydrocarbon group, and $R^{9a}$ and $R^{8b}$ may bond together to form a $C_3$-$C_8$ non-aromatic ring with the carbon atom to which they are attached. $R^{9a}$ is a straight, branched or cyclic, $C_1$-$C_{15}$ monovalent fluorinated hydrocarbon group. $R^{10a}$ is a straight, branched or cyclic, $C_1$-$C_{15}$ monovalent hydrocarbon or fluorinated hydrocarbon group. $R^{11a}$ is a straight, branched or cyclic, $C_1$-$C_{10}$ monovalent fluorinated hydrocarbon group. $R^{12a}$ is hydrogen or a straight, branched or cyclic, $C_1$-$C_{20}$ monovalent hydrocarbon group in which any constituent moiety —$CH_2$— may be replaced by —O— or —C(=O)—. A is a straight, branched or cyclic, ($k^2$+1)-valent hydrocarbon or fluorinated hydrocarbon group of 1 to 20 carbon atoms. The subscript $k^1$ is 0 or 1, and $k^2$ is 1, 2 or 3.

The present polymer preferably has a weight average molecular weight (Mw) of 3,000 to 200,000, and preferably 3,000 to 20,000, as measured by GPC versus polystyrene standards using tetrahydrofuran solvent. Outside the range, a polymer with too low a Mw may be miscible with the resist material and soluble in water whereas a polymer with too high a Mw may be awkward to form a film by spin coating and less alkali soluble.

As described above, using the present fluorinated ester monomer (1) alone or in combination with at least one other monomer, a homopolymer or a copolymer may be prepared by standard techniques such as radical polymerization, anionic polymerization or cationic polymerization. The preparation method and conditions may be any of well-known methods and conditions used in the polymerization of polymerizable unsaturated bonds, typically polymerizable double bonds.

The fluorinated ester monomer of the invention is best suited to produce a polymer for use as an additive to an immersion lithography resist material or as a material for forming a resist protective film on a resist film of immersion lithography resist material. As used herein, the term "immersion lithography" refers to lithography in which a resist film is exposed to radiation from a projection lens while a high refractive index liquid having a refractive index of at least 1 such as water or alkane is interposed between the projection lens and the resist film.

Once a polymer is prepared from the fluorinated ester monomer, the polymer is added to an immersion lithography resist material to form a resist composition. The resist composition may be used to form a photoresist film which has a sufficient barrier function against water to prevent the photoresist material from being dissolved in water. This eliminates a need for a protective film in the immersion lithography and saves the cost required in formation of a protective film. In addition, the photoresist film has so great a receding contact angle with water that few droplets may be left on the photoresist film surface after scanning with exposure light by the immersion lithography, substantially avoiding any pattern formation failure caused by droplets left on the film surface.

The present polymer is also useful as a material for forming a resist protective film on a resist film of immersion lithography resist material for protecting the resist film during liquid immersion. When the present polymer is used as a resist protective film-forming material, the resulting protective film has a high receding contact angle with water enough to restrain dissolution of resist components and penetration of water. Then the immersion lithography can be implemented so as to form a resist pattern of satisfactory profile after development without substantial development defects.

Understandably, the method for preparing a polymer from the present monomer may be any of conventional polymerization methods including radical polymerization using an initiator such as 2,2'-azobisisobutyronitrile (AIBN), and ionic, typically anionic, polymerization using alkyllithium or the like. Such polymerization may be carried out by the standard technique. Inter alia, radical polymerization is preferred for polymer preparation. Suitable polymerization conditions may be selected depending on the type and amount of initiator, temperature, pressure, concentration, solvent, additive and the like.

The radical polymerization initiator used herein is not particularly limited. Suitable initiators include azo compounds such as AIBN, 2,2'-azobis(4-methoxy-2,4-dimethylvaleronitrile), 2,2'-azobis(2,4-dimethylvaleronitrile), 2,2'-azobis(2,4,4-trimethylpentane), and dimethyl 2,2'-azobis(isobutyrate), peroxides such as tert-butyl peroxypivalate, lauroyl peroxide, benzoyl peroxide, and tert-butyl peroxylaurate, water-soluble polymerization initiators such as potassium persulfate, and redox initiators in the form of a combination of a peroxide (e.g., potassium persulfate or hydrogen peroxide) with a reducing agent (e.g., sodium sulfite). An amount of the initiator used varies with its type and polymerization conditions and is usually 0.001 to 10 mol %, preferably 0.01 to 6 mol % based on the total amount of monomers to be polymerized.

Polymerization may be conducted in a solvent, if desired. Preferred is the solvent which does not interfere with polymerization. Typical solvents include esters such as ethyl acetate, n-butyl acetate and γ-butyrolactone, ketones such as acetone, methyl ethyl ketone, and methyl isobutyl ketone, aliphatic or aromatic hydrocarbons such as toluene, xylene and cyclohexane, alcohols such as isopropyl alcohol and ethylene glycol monomethyl ether, and ethers such as diethyl ether, dioxane, and tetrahydrofuran. These solvents may be used alone or in admixture. An amount of the solvent used may vary with the desired degree of polymerization (or molecular weight), the amount of initiator added, and polymerization conditions such as temperature. Usually an amount of the solvent is used to form a reaction solution having a concentration of 0.1 to 95 wt %, preferably 5 to 90 wt % of the monomers to be polymerized.

The reaction temperature may vary with the type of initiator or the boiling point of the solvent. Usually the temperature preferably ranges from 20° C. to 200° C., more preferably from 50° C. to 140° C. The type of reactor used in such polymerization reaction is not particularly limited.

From the resulting polymer solution or dispersion, the organic solvent as the reaction medium or water may be removed by any well-known techniques, for example, re-precipitation and filtration, or vacuum distillation at elevated temperature.

When the present polymer is formulated into a resist material, the resist material may be any well-known composition. The present polymer (or additive polymer) is mixed with a base resin to be described below. When the resulting resist material is spin coated to form a resist film, they undergo layer separation so that the present polymer is segregated as an upper layer of the resist film. The polymer segregated serves to improve water repellency and water slip on the resist film surface and prevents any water-soluble compound from being leached out of the resist material.

The resist material used herein contains as a base resin a polymer comprising recurring units having lactone ring and/or hydroxyl group and/or recurring units having a structure derived from maleic anhydride, the polymer turning soluble in alkaline developer under the action of acid. Examples of the polymer used as base resin include (meth)acrylate polymers, α-trifluoromethyl acrylate/maleic anhydride copolymers, cycloolefin/maleic anhydride alternating copolymers, polynorbornene, cycloolefin ring-opening metathesis polymerization (ROMP) polymers, and hydrogenated cycloolefin ROMP polymers. Specific polymers are described in JP-A 2008-111103, paragraph [0072] to [0120] (U.S. Pat. No. 7,537,880). The polymer as base resin is not limited to one type and a mixture of two or more polymers may be added. The use of plural polymers allows for easy adjustment of resist properties.

In order that the resist material function as a chemically amplified positive resist material, the resist material contains a photoacid generator (PAG), i.e., a compound capable of generating an acid upon exposure of high-energy radiation. Suitable PAGs include sulfonium salt, iodonium salt, sulfonyldiazomethane, N-sulfonyloxyimide, and oxime-O-sulfonate acid generators. Exemplary acid generators are described in JP-A 2008-111103, paragraph [0123] to [0138]. An appropriate amount of PAG added is 0.1 to 20 parts, and more preferably 0.1 to 10 parts by weight per 100 parts by weight of the base resin in the resist material. As long as PAG is up to 20 phr, the resulting photoresist film has a fully high transmittance and a minimal likelihood of degraded resolution. The PAG may be used alone or in admixture of two or more. The transmittance of the resist film can be controlled by using a PAG having a low transmittance at the exposure wavelength and adjusting the amount of the PAG added.

The resist material may further comprise an organic solvent, basic compound, dissolution regulator, surfactant, and acetylene alcohol, wherein each may be used alone or in admixture of two or more.

An amount of the present polymer added to the resist material may be 0.1 to 50 parts by weight per 100 parts by weight of the base resin.

The immersion lithography using the resist material may be any well-known one.

When the present polymer is used as a resist protective film-forming material, the composition of the resist material and the immersion lithography are as described above, and the resist protective film-forming material may be used in accordance with any well-known embodiments and methods.

EXAMPLE

Examples are given below by way of illustration and not by way of limitation. Mw and Mn are weight and number average molecular weights, respectively, as measured in tetrahydrofuran solvent by GPC versus polystyrene standards. Me stands for methyl, and Et for ethyl.

Example 1

Synthesis of 2,2-difluoro-3-hydroxy-5-methylhexanoic acid (Intermediate 1)

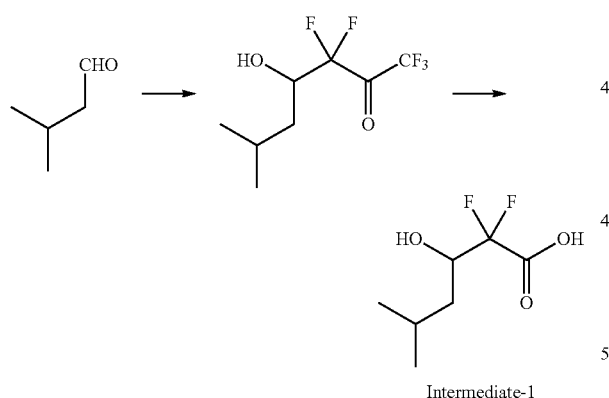

Intermediate-1

With stirring in a nitrogen atmosphere, a mixture of 111 g of 1,1,1,3,3,3-hexafluoro-2-propanol and 700 ml of tetrahydrofuran was cooled below −40° C., to which 500 ml of a n-hexane solution of 2.64M n-butyllithium was added dropwise. At the temperature, the reaction mixture was stirred for 30 minutes. The cooling bath was changed to ice cooling, allowing the reaction mixture to warm to 5° C. A mixture of 50 g of isovaleraldehyde and 50 ml of tetrahydrofuran was added dropwise. With stirring, the reaction mixture was warmed up to room temperature, after which stirring was continued for a further 5 hours. The reaction mixture was poured into dilute hydrochloric acid and extracted with ether. The ether solution was washed, dried, and concentrated, obtaining crude 1,1,1,3,3-pentafluoro-4-hydroxy-2-heptanone. The crude product was combined with 50 g of water at room temperature, to which 100 g of 25 wt % sodium hydroxide aqueous solution was added. The mixture was stirred overnight at room temperature. With stirring, the mixture was slowly heated to 90° C. After cooling, the reaction mixture was extracted with n-hexane, with the hexane layer being discarded. The water layer was made acidic by adding 20 wt % hydrochloric acid, and extracted with ethyl acetate. The ethyl acetate solution was dried and concentrated, obtaining 107 g (qualitative yield) of the target compound, 2,2-difluoro-3-hydroxy-5-methylhexanoic acid (Intermediate 1). This crude product had a sufficient purity as an intermediate and was ready for use in the subsequent step.

2,2-difluoro-3-hydroxy-5-methylhexanoic acid

Pale Yellow Solid
IR (D-ATR): ν=3311, 2966, 1725, 1472, 1404, 1276, 1211, 1131, 1117, 1074, 979, 919 cm$^{-1}$
$^1$H-NMR (600 MHz in DMSO-d$_6$): δ=0.84 (3H, d, J=6.4 Hz), 0.90 (3H, d, J=6.4 Hz), 1.17 (1H, br. app t, J=12 Hz), 1.41-1.47 (1H, m), 1.72-1.81 (1H, m), 3.84-3.92 (1H, m), 5.10-6.10 (1H, br., OH), 13.4-15.0 (1H, COOH) ppm
$^{13}$C-NMR (150 MHz in DMSO-d$_6$): δ=21.02, 23.41, 23.57, 37.62 (d, J=3 Hz), 68.00 (dd, J=25, 26 Hz), 115.6 (dd, J=251, 256 Hz), 165.0 (dd, J=30, 32 Hz) ppm
$^{19}$F-NMR (564 MHz in DMSO-d$_6$, trifluoroacetic acid standard—same hereinafter—): δ=−122.53 (1F, dd, J=16, 250 Hz), −116.04 (1F, dd, J=8.7, 250 Hz) ppm Example 2

Synthesis of 2,2-difluoro-3-hydroxy-4-methylpentanoic acid (Intermediate 2)

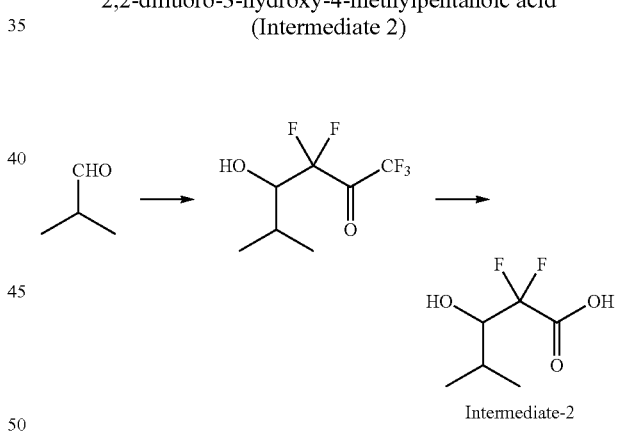

Intermediate-2

By the same procedure as Example 1 aside from using isobutyl aldehyde instead of isovaleraldehyde, the target compound, 2,2-difluoro-3-hydroxy-4-methylpentanoic acid (Intermediate 2) was obtained (yield 93%). This crude product had a sufficient purity as an intermediate and was ready for use in the subsequent step.

2,2-difluoro-3-hydroxy-4-methylpentanoic acid

Pale Yellow Solid
IR (D-ATR): ν=3311, 2966, 1732, 1474, 1401, 1296, 1208, 1125, 1053, 933, 916 cm$^{-1}$
$^1$H-NMR (600 MHz in DMSO-d$_6$): δ=0.87 (3H, d, J=7.3 Hz), 0.90 (3H, d, J=6.4 Hz), 1.79-1.90 (1H, m), 3.58-3.67 (1H, m), 5.10-6.20 (1H, br., OH), 13.4-15.0 (1H, COOH) ppm $^{13}$C-NMR (150 MHz in DMSO-d$_6$): δ=17.50, 19.74, 28.28, 73.52 (dd, J=22, 25 Hz), 116.3 (dd, J=253, 257 Hz), 165.2 (app t, J=31 Hz) ppm $^{19}$F-NMR (564 MHz in DMSO-d$_6$): δ=−122.55 (1F, dd, J=18, 253 Hz), −112.53 (1F, dd, J=9.0, 253 Hz) ppm Example 3

Synthesis of
2,2-difluoro-3-hydroxy-3-methylbutanoic acid
(Intermediate 3)

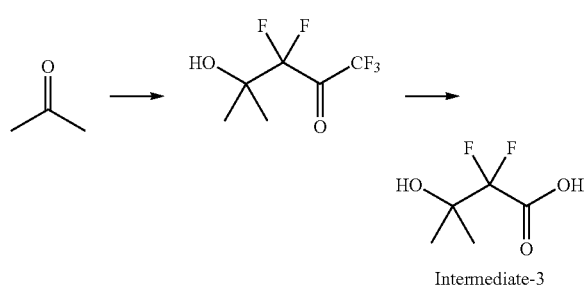

Intermediate-3

By the same procedure as Example 1 aside from using acetone instead of isovaleraldehyde, the target compound, 2,2-difluoro-3-hydroxy-3-methylbutanoic acid (Intermediate 3) was obtained (yield 78%). This crude product had a sufficient purity as an intermediate and was ready for use in the subsequent step.

2,2-difluoro-3-hydroxy-3-methylbutanoic acid

Pale Yellow Solid

IR (D-ATR): ν=3367, 3194, 2995, 2664, 2548, 1739, 1460, 1378, 1300, 1206, 1137, 1110, 1064, 975 cm$^{-1}$ $^1$H-NMR (600 MHz in DMSO-d$_6$): δ=1.22 (3H, s), 4.50-5.60 (1H, br., OH), 11.5-15.5 (1H, COOH) ppm $^{13}$C-NMR (150 MHz in DMSO-d$_6$): δ=23.56 (2C, t, J=2.9 Hz), 71.00 (t, J=24.5 Hz), 116.66 (t, J=256 Hz), 164.88 (t, J=31 Hz) ppm $^{19}$F-NMR (564 MHz in DMSO-d$_6$): δ=−117.80 (2F, s) ppm Example 4

Synthesis of 2,2-difluoro-3-hydroxyhexanoic acid
(Intermediate 4)

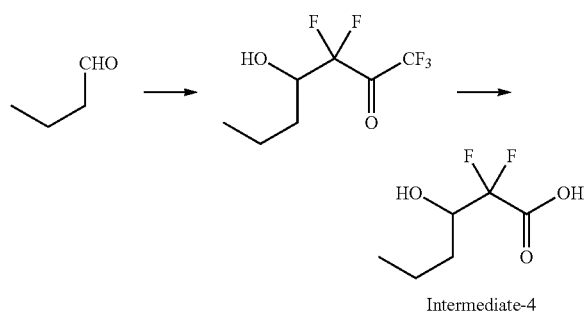

Intermediate-4

By the same procedure as Example 1 aside from using butyl aldehyde instead of isovaleraldehyde, the target compound, 2,2-difluoro-3-hydroxyhexanoic acid (Intermediate 4) was obtained (yield 75%). This crude product had a sufficient purity as an intermediate and was ready for use in the subsequent step.

2,2-difluoro-3-hydroxyhexanoic acid

Pale Yellow Solid

IR (D-ATR): ν=3341, 2966, 2690, 2550, 1739, 1464, 1308, 1274, 1259, 1210, 1113, 1081, 1061 cm$^{-1}$ $^1$H-NMR (600 MHz in DMSO-d$_6$): δ=0.87 (3H, t, J=7.2 Hz), 1.26-1.37 (1H, m), 1.39-1.45 (2H, m), 1.45-1.54 (1H, m), 3.77-3.88 (1H, m), 4.70-6.30 (1H, br., OH), 12.5-15.6 (1H, COOH) ppm $^{13}$C-NMR (150 MHz in DMSO-d$_6$): δ=13.66, 18.05, 30.93 (d, J=3 Hz), 69.43 (dd, J=24, 27 Hz), 115.61 (dd, J=251, 256 Hz), 165.01 (t, J=31 Hz) ppm $^{19}$F-NMR (564 MHz in DMSO-d$_6$): δ=−122.53 (1F, dd, J=16, 250 Hz), −115.68 (1F, J=8.6, 250 Hz) ppm Example 5

Synthesis of methyl
2,2-difluoro-3-methacryloyloxy-5-methylhexanoate
(Monomer 1)

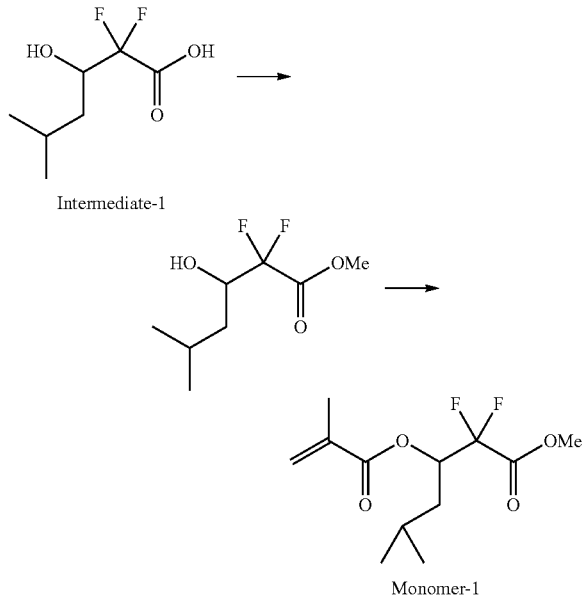

Monomer-1

Example 5-1

Synthesis of methyl
2,2-difluoro-3-hydroxy-5-methylhexanoate

To a mixture of 28.11 g of Intermediate 1 (Example 1) and 280 g of methanol was added 0.6 g of p-toluenesulfonic acid monohydrate. With stirring in a nitrogen atmosphere, the mixture was heated under reflux for 8 hours. After cooling, the reaction mixture was concentrated to about 200 ml. The concentrate was poured into a saturated sodium hydrogen carbonate aqueous solution and extracted with ether. The ether solution was washed, dried, and concentrated, obtaining 21.8 g (yield 72%) of methyl 2,2-difluoro-3-hydroxy-5-methylhexanoate. This crude product had a sufficient purity as an intermediate and was ready for use in the subsequent step.

methyl 2,2-difluoro-3-hydroxy-5-methylhexanoate

Yellow Liquid
IR (D-ATR): ν=3461, 2961, 2874, 1763, 1470, 1443, 1317, 1273, 1214, 1128, 1070 cm$^{-1}$
$^1$H-NMR (600 MHz in DMSO-d$_6$): δ=0.85 (3H, d, J=6.4 Hz), 0.91 (3H, d, J=6.4 Hz), 1.20 (1H, br. app t, J=12 Hz), 1.41-1.47 (1H, m), 1.72-1.81 (1H, m), 3.82 (3H, s), 3.82-3.95 (1H, m), 5.79 (1H, br., OH) ppm Example 5-2

Synthesis of methyl 2,2-difluoro-3-methacryloyloxy-5-methylhexanoate (Monomer 1)

With stirring at room temperature in a nitrogen atmosphere, 13.0 g of triethylamine was added dropwise to a mixture of 18.4 g of crude methyl 2,2-difluoro-3-hydroxy-5-methylhexanoate, 13.0 g of methacryloyl chloride, and 150 ml of acetonitrile. The reaction mixture was stirred overnight at room temperature. Thereafter, 15 ml of water, 10 ml of triethylamine, and a catalytic amount of 4-dimethylaminopyridine were successively added to the reaction mixture, which was stirred for a further 2 hours at room temperature. The reaction mixture was poured into water and extracted with a hexane/ether mixture. The solution was washed, dried, and concentrated. The residue was distilled in vacuum, obtaining 13.6 g (yield 62%) of the target compound, methyl 2,2-difluoro-3-methacryloyloxy-5-methylhexanoate (Monomer Monomer 1: methyl 2,2-difluoro-3-methacryloyloxy-5-methylhexanoate Colorless Liquid
Boiling Point: 57° C./20 Pa
IR (D-ATR): ν=2962, 1771, 1732, 1440, 1316, 1294, 1154, 1127, 1080, 975 cm$^{-1}$
$^1$H-NMR (600 MHz in DMSO-d$_6$): δ=0.87 (3H, t, J=6.4 Hz), 0.90 (3H, d, J=6.9 Hz), 1.45-1.51 (1H, m), 1.52-1.60 (1H, m), 1.65-1.71 (1H, m), 1.89 (3H, br. s), 3.84 (3H, s), 5.39-5.47 (1H, m), 5.79 (1H, app q, J=1.5 Hz), 6.07 (1H, app t, J=1.2 Hz) ppm
$^{13}$C-NMR (150 MHz in DMSO-d$_6$): δ=17.69, 20.99, 22.81, 23.61, 35.39, 54.01, 69.38 (app t, J=25 Hz), 113.37 (t, J=255 Hz), 127.54, 134.59, 162.35 (t, J=31 Hz), 165.29 ppm
$^{19}$F-NMR (564 MHz in DMSO-d$_6$): δ=−117.50 (1F, ddd, J=4, 12, 258 Hz), −115.76 (1F, dd, J=11, 258 Hz) ppm Example 6

Synthesis of ethyl 2,2-difluoro-3-methacryloyloxy-5-methylhexanoate (Monomer 2)

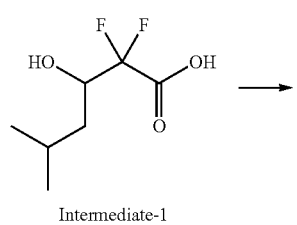

Intermediate-1

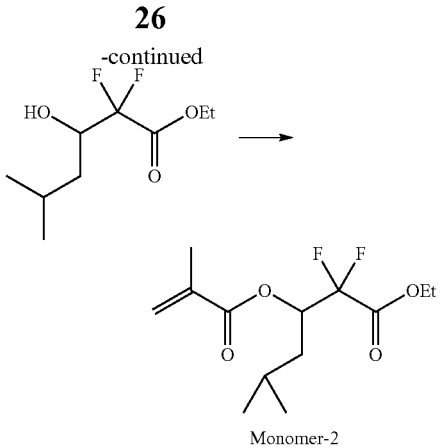

Monomer-2

Example 6-1

Synthesis of ethyl 2,2-difluoro-3-hydroxy-5-methylhexanoate

To a mixture of 25.0 g of Intermediate 1 (Example 1), 20 g of ethanol and 200 g of benzene was added 0.15 g of p-toluenesulfonic acid monohydrate. With stirring in a nitrogen atmosphere, the mixture was heated for 20 hours while water of reaction was sequentially removed out of the system. After cooling, the reaction mixture was poured into a saturated sodium hydrogen carbonate aqueous solution and extracted with ethyl acetate. The ethyl acetate solution was washed, dried, and concentrated, obtaining 24.5 g (yield 85%) of crude ethyl 2,2-difluoro-3-hydroxy-5-methylhexanoate. This crude product had a sufficient purity as an intermediate and was ready for use in the subsequent step.

ethyl 2,2-difluoro-3-hydroxy-5-methylhexanoate

Pale Yellow Liquid
IR (D-ATR): ν=3466, 2961, 2874, 1760, 1470, 1373, 1314, 1272, 1214, 1129, 1069 cm$^{-1}$
$^1$H-NMR (600 MHz in DMSO-d$_6$): δ=0.85 (3H, d, J=6.3 Hz), 0.91 (3H, d, J=6.8 Hz), 1.16-1.22 (1H, m), 1.25 (3H, t, J=7.1 Hz), 1.41-1.47 (1H, m), 1.73-1.82 (1H, m), 3.85-3.94 (1H, m), 4.22-4.33 (1H, m), 5.77 (1H, br., OH) ppm
$^{19}$F-NMR (564 MHz in DMSO-d$_6$): δ=−122.65 (1F, dd, J=16.3, 252 Hz), −114.98 (1F, dd, J=8.7, 251 Hz) ppm Example 6-2

Synthesis of ethyl 2,2-difluoro-3-methacryloyloxy-5-methylhexanoate (Monomer 2)

With stirring at room temperature in a nitrogen atmosphere, 20.5 g of triethylamine was added dropwise to a mixture of 27.1 g of crude ethyl 2,2-difluoro-3-hydroxy-5-methylhexanoate, 20.5 g of methacryloyl chloride, and 200 ml of acetonitrile. The reaction mixture was stirred overnight at room temperature. Thereafter, 15 ml of water, 10 ml of triethylamine, and a catalytic amount of 4-dimethylaminopyridine were successively added to the reaction mixture, which was stirred for a further 2 hours at room temperature. The reaction mixture was poured into water and extracted with a hexane/ether mixture. The solution was washed, dried, and concentrated. The residue was distilled in vacuum, obtaining 30.5 g (yield 85%) of the target compound, ethyl 2,2-difluoro-3-methacryloyloxy-5-methylhexanoate (Monomer 2).

Monomer 2: ethyl 2,2-difluoro-3-methacryloyloxy-5-methylhexanoate

Colorless Liquid
Boiling Point: 67-68° C./60 Pa
IR (D-ATR): ν=2963, 1773, 1732, 1313, 1221, 1154, 1127, 1079 cm$^{-1}$
$^1$H-NMR (600 MHz in DMSO-d$_6$): δ=0.88 (3H, d, J=6.4 Hz), 0.90 (3H, d, J=6.4 Hz), 1.22 (3H, t, J=7.1 Hz), 1.45-1.50 (1H, m), 1.51-1.59 (1H, m), 1.65-1.71 (1H, m), 1.88 (3H, br. s), 4.28 (2H, app q, J=6.8 Hz), 5.40-5.48 (1H, m), 5.79 (1H, app q, J=1.5 Hz), 6.08 (1H, br. s) ppm
$^{13}$C-NMR (150 MHz in DMSO-d$_6$): δ=13.53, 17.67, 21.02, 22.84, 23.59, 35.46, 63.46, 69.35 (dd, J=25, 29 Hz), 113.30 (t, J=255 Hz), 127.57, 134.60, 161.79 (t, J=32 Hz), 165.23 ppm
$^{19}$F-NMR (564 MHz in DMSO-d$_6$): δ=-118.04 (1F, dd, J=12, 258 Hz), -115.33 (1F, dd, J=11, 258 Hz) ppm Example 7

Synthesis of 2-methoxyethyl 2,2-difluoro-3-methacryloyloxy-5-methylhexanoate (Monomer 3)

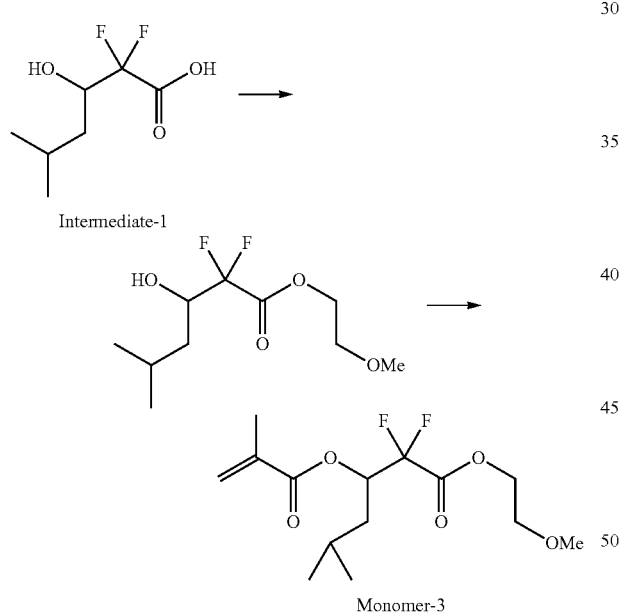

Example 7-1

Synthesis of 2-methoxyethyl 2,2-difluoro-3-hydroxy-5-methylhexanoate

To a mixture of 25.0 g of Intermediate 1 (Example 1), 25 g of 2-methoxyethanol and 200 g of benzene was added 0.15 g of p-toluenesulfonic acid monohydrate. With stirring in a nitrogen atmosphere, the mixture was heated for 8 hours while water of reaction was sequentially removed out of the system. After cooling, the reaction mixture was poured into ice water and extracted with ether. The ether solution was washed, dried, and concentrated, obtaining 23.9 g (yield 73%) of crude 2-methoxyethyl 2,2-difluoro-3-hydroxy-5-methylhexanoate. This crude product had a sufficient purity as an intermediate and was ready for use in the subsequent step.

2-methoxyethyl 2,2-difluoro-3-hydroxy-5-methylhexanoate

Pale Yellow Liquid
IR (D-ATR): ν=3424, 2960, 2874, 1771, 1470, 1372, 1310, 1204, 1129, 1085, 1068 cm$^{-1}$
$^1$H-NMR (600 MHz in DMSO-d$_6$): δ=0.85 (3H, d, J=6.4 Hz), 0.91 (3H, d, J=6.8 Hz), 1.15-1.22 (1H, m), 1.41-1.48 (1H, m), 1.73-1.82 (1H, m), 3.26 (3H, s), 3.53-3.61 (2H, m), 3.85-3.95 (1H, m), 4.29-4.43 (2H, m), 5.77 (1H, br., OH) ppm
$^{13}$C-NMR (150 MHz in DMSO-d$_6$): δ=20.92, 23.37, 23.48, 37.41, 58.04, 65.39, 68.17 (t, J=25 Hz), 69.22, 115.69 (dd, J=253, 256 Hz), 163.36 (t, J=32 Hz) ppm
$^{19}$F-NMR (564 MHz in DMSO-d$_6$): δ=-121.44 (1F, dd, J=15.2, 253 Hz), -115.89 (1F, dd, J=9.7, 253 Hz) ppm Example 7-2

Synthesis of 2-methoxyethyl 2,2-difluoro-3-methacryloyloxy-5-methylhexanoate (Monomer-3)

With stirring at room temperature in a nitrogen atmosphere, 18.5 g of triethylamine was added dropwise to a mixture of 23.7 g of crude 2-methoxyethyl 2,2-difluoro-3-hydroxy-5-methylhexanoate, 18.5 g of methacryloyl chloride, and 200 ml of acetonitrile. The reaction mixture was stirred overnight at room temperature. Thereafter, 15 ml of water, 10 ml of triethylamine, and a catalytic amount of 4-dimethylaminopyridine were successively added to the reaction mixture, which was stirred for a further 2 hours at room temperature. The reaction mixture was poured into water and extracted with a hexane/ether mixture. The solution was washed, dried, and concentrated. The residue was distilled in vacuum, obtaining 23.2 g (yield 76%) of the target compound, 2-methoxyethyl 2,2-difluoro-3-methacryloyloxy-5-methylhexanoate (Monomer 3).

Monomer 3: 2-methoxyethyl 2,2-difluoro-3-methacryloyloxy-5-methylhexanoate

Yellow Liquid
Boiling Point: 102° C./80 Pa
IR (D-ATR): ν=2962, 1774, 1731, 1312, 1293, 1155, 1129, 1079 cm$^{-1}$
$^1$H-NMR (600 MHz in DMSO-d$_6$): δ=0.88 (3H, d, J=6.4 Hz), 0.90 (3H, d, J=6.8 Hz), 1.43-1.50 (1H, m), 1.51-1.59 (1H, m), 1.65-1.71 (1H, m), 1.88 (3H, br. s), 3.24 (3H, s), 3.52-3.59 (2H, m), 4.35-4.44 (2H, m), 5.40-5.48 (1H, m), 5.79 (1H, app t, J=1.5 Hz), 6.09 (1H, br. s) ppm
$^{13}$C-NMR (150 MHz in DMSO-d$_6$): δ=17.69, 20.95, 22.85, 23.58, 35.55, 57.91, 65.95, 69.05, 69.33 (t, J=25 Hz), 113.45 (t, J=255 Hz), 127.50, 134.63, 161.76 (t, J=31 Hz), 165.26 ppm
$^{19}$F-NMR (564 MHz in DMSO-d$_6$): δ=-116.71 (1F, dd, J=11, 258 Hz), -116.07 (1F, dd, J=11, 258 Hz) ppm

Example 8

Synthesis of 2,2-difluoro-3-methacryloyloxy-5-methylhexanoic acid (Monomer 4)

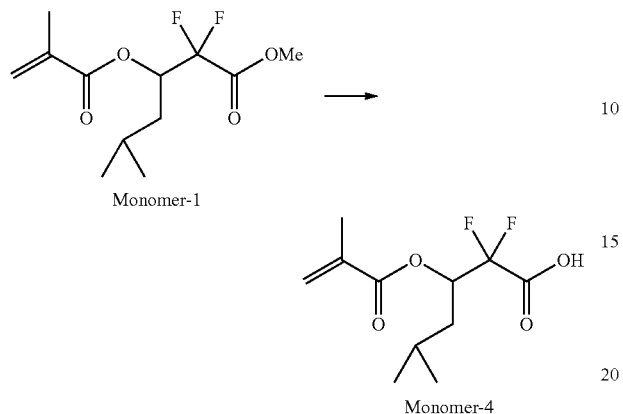

With stirring, a mixture of 15.6 g of Monomer-1 (Example 5) and 50 ml of diglyme was ice cooled, to which 50.0 g of 5 wt % sodium hydroxide aqueous solution was added dropwise below 15° C. After stirring for 30 minutes, the reaction mixture was extracted with n-hexane. After the hexane layer was discarded, 20 g of 20 wt % hydrochloric acid was added to the water layer to make it acidic, followed by extraction with diisopropyl ether. The diisopropyl ether solution was washed, dried, concentrated, and vacuum distilled, obtaining 14.6 g (yield 99%) of 2,2-difluoro-3-methacryloyloxy-5-methylhexanoic acid.

Monomer 4: 2,2-difluoro-3-methacryloyloxy-5-methylhexanoic acid

Yellow Liquid
Boiling Point: 118° C./80 Pa
IR (D-ATR): ν=3512, 2963, 1760, 1732, 1314, 1296, 1158, 1128, 1080 cm$^{-1}$
$^1$H-NMR (600 MHz in DMSO-d$_6$): δ=0.87 (3H, d, J=6.3 Hz), 0.89 (3H, d, J=6.3 Hz), 1.41-1.47 (1H, m), 1.49-1.59 (1H, m), 1.65-1.70 (1H, m), 1.88 (3H, br. s), 5.40-5.48 (1H, m), 5.77 (1H, app t, J=1.8 Hz), 6.07 (1H, br. s) ppm
$^{13}$C-NMR (150 MHz in DMSO-d$_6$): δ=17.71, 21.11, 22.94, 23.64, 35.82, 69.41 (t, J=26 Hz), 113.55 (t, J=254 Hz), 127.34, 134.81, 163.57 (t, J=30 Hz), 165.38 ppm
$^{19}$F-NMR (564 MHz in DMSO-d$_6$): δ=−117.66 (1F, dd, J=12, 256 Hz), −116.73 (1F, dd, J=12, 256 Hz) ppm

Example 9

Synthesis of methyl 2,2-difluoro-3-methacryloyloxy-4-methylpentanoate (Monomer 5)

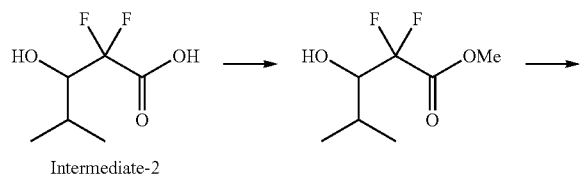

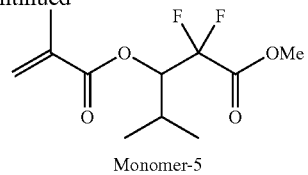

Example 9-1

Synthesis of methyl 2,2-difluoro-3-hydroxy-4-methylpentanoate

To a mixture of 50 g of Intermediate 2 (Example 2), 200 g of methanol and 250 g of benzene was added 0.3 g of p-toluenesulfonic acid monohydrate. With stirring in a nitrogen atmosphere, the mixture was heated under reflux for 20 hours. After cooling, the reaction mixture was poured into a saturated sodium hydrogen carbonate aqueous solution and extracted with hexane. The hexane solution was washed, dried, and concentrated, obtaining 45.78 g (yield 85%) of methyl 2,2-difluoro-3-hydroxy-4-methylpentanoate. This crude product had a sufficient purity as an intermediate and was ready for use in the subsequent step.

methyl 2,2-difluoro-3-hydroxy-4-methylpentanoate

Yellow Liquid
IR (D-ATR): ν=3480, 2966, 2882, 1764, 1443, 1325, 1214, 1109, 1058 cm$^{-1}$
$^1$H-NMR (600 MHz in DMSO-d$_6$): δ=0.91 (3H, d, J=6.9 Hz), 0.93 (3H, dd, J=1.4, 6.9 Hz), 1.81-1.90 (1H, m), 3.58-3.68 (1H, m), 3.81 (3H, s), 5.83 (1H, br., OH) ppm
$^{13}$C-NMR (150 MHz in DMSO-d$_6$): δ=17.57, 19.46, 28.19, 53.28, 73.65 (dd, J=23, 26 Hz), 116.42 (dd, J=252, 259 Hz), 164.05 (dd, J=31, 33 Hz) ppm
$^{19}$F-NMR (564 MHz in DMSO-d$_6$): δ=−121.65 (1F, dd, J=20, 254 Hz), −110.46 (1F, dd, J=8, 254 Hz) ppm

Example 9-2

Synthesis of methyl 2,2-difluoro-3-methacryloyloxy-4-methylpentanoate (Monomer 5)

With stirring at room temperature in a nitrogen atmosphere, 28.4 g of triethylamine was added dropwise to a mixture of 29.24 g of methyl 2,2-difluoro-3-hydroxy-4-methylpentanoate, 28.4 g of methacryloyl chloride, and 300 ml of acetonitrile. The reaction mixture was stirred overnight at room temperature. Thereafter, 30 ml of water, 20 ml of triethylamine, and a catalytic amount of 4-dimethylaminopyridine were successively added to the reaction mixture, which was stirred for a further 1 hours at room temperature. The reaction mixture was poured into water and extracted with a hexane/ether mixture. The solution was washed, dried, and concentrated. The residue was distilled in vacuum, obtaining 54.8 g (yield 81%) of the target compound, methyl 2,2-difluoro-3-methacryloyloxy-4-methylpentanoate (Monomer 5).

Monomer 5: methyl 2,2-difluoro-3-methacryloyloxy-4-methylpentanoate

Colorless Liquid

Boiling Point: 55° C./25 Pa

IR (D-ATR): ν=2972, 1771, 1732, 1441, 1319, 1220, 1154, 1116, 1084, 1062 cm$^{-1}$ $^1$H-NMR (600 MHz in DMSO-d$_6$): δ=0.92 (3H, d, J=6.9 Hz), 0.95 (3H, d, J=6.9 Hz), 1.90 (3H, br. s), 2.10-2.19 (1H, m), 3.82 (3H, s), 5.18-5.25 (1H, m), 5.78-5.82 (1H, m), 6.09 (1H, br. s) ppm $^{13}$C-NMR (150 MHz in DMSO-d$_6$): δ=17.02, 17.73, 19.11, 27.28, 53.99, 74.18 (dd, J=23, 28 Hz), 113.83 (t, J=256 Hz), 127.48, 134.63, 162.60 (t, J=31 Hz), 165.22 ppm $^{19}$F-NMR (564 MHz in DMSO-d$_6$): δ=-115.03 (1F, dd, J=15, 260 Hz), -112.86 (1F, dd, J=11, 260 Hz) ppm

Example 10

Synthesis of 2,2-difluoro-3-methacryloyloxy-4-methylpentanoic acid (Monomer 6)

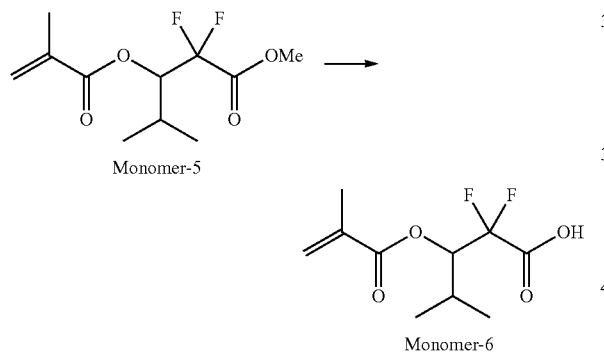

The same procedure as Example 8 was repeated aside from using Monomer 5 (Example 9) instead of Monomer 1 in Example 8, obtaining the target compound, 2,2-difluoro-3-methacryloyloxy-4-methylpentanoic acid in a yield of 75%.

Monomer 6: 2,2-difluoro-3-methacryloyloxy-4-methylpentanoic acid

Yellow Liquid

Boiling Point: 94° C./30 Pa

IR (D-ATR): ν=3198, 2974, 1770, 1733, 1705, 1304, 1159, 1059 cm$^{-1}$ $^1$H-NMR (600 MHz in DMSO-d$_6$): δ=0.92 (3H, d, J=6.9 Hz), 0.95 (3H, d, J=6.9 Hz), 1.89 (3H, app t, J=1.5 Hz), 2.08-2.17 (1H, m), 5.18-5.26 (1H, m), 5.77 (1H, app quint, J=1.2 Hz), 6.09 (1H, br. s), 12.5-15.5 (1H, br., OH) ppm $^{13}$C-NMR (150 MHz in DMSO-d$_6$): δ=17.16, 17.80, 19.27, 27.45, 74.26 (app t, J=26 Hz), 113.99 (t, J=255 Hz), 127.24, 134.86, 163.83 (t, J=30 Hz), 165.32 ppm $^{19}$F-NMR (564 MHz in DMSO-d$_6$): δ=-114.89 (1F, dd, J=14, 257 Hz), -113.86 (1F, dd, J=12, 257 Hz) ppm

Example 11

Synthesis of 2,2,3,3,4,4,5,5-octafluoropentyl 2,2-difluoro-3-methacryloyloxy-4-methylpentanoate (Monomer 7)

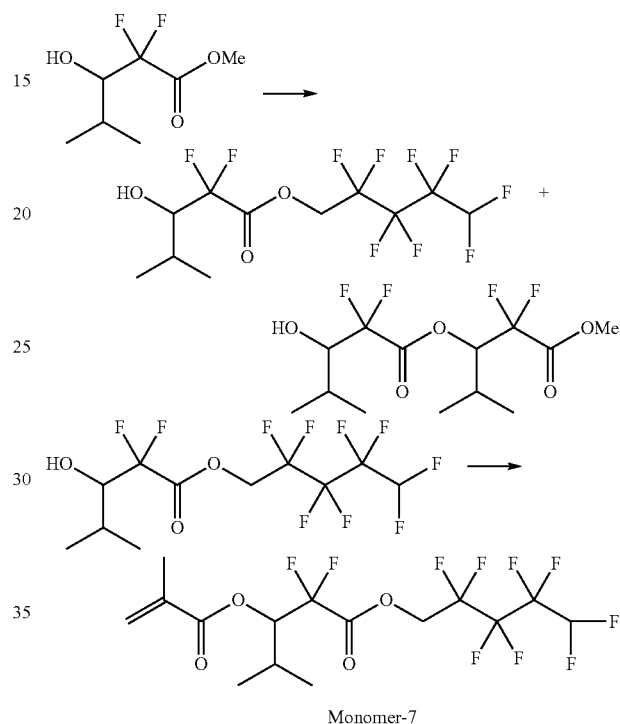

Example 11-1

Synthesis of 2,2,3,3,4,4,5,5-octafluoropentyl 2,2-difluoro-3-hydroxy-4-methylpentanoate and methyl 2,2-difluoro-3-(2,2-difluoro-3-hydroxy-4-methylpentanoyloxy)-4-methylpentanoate A catalytic amount of potassium t-butoxide was added to a mixture of 46.8 g of methyl 2,2-difluoro-3-hydroxy-4-methylpentanoate (synthesized in Example 9-1) and 200 g of 2,2,3,3,4,4,5,5-octafluoro-1-pentanol. With stirring in a nitrogen atmosphere, the mixture was heated under reflux for 48 hours while a fraction distilled below 100-115° C. was sequentially removed out of the system. After cooling, the reaction mixture was filtered through a silica gel filter and distilled in vacuum, recovering part of 2,2,3,3,4,4,5,5-octafluoro-1-pentanol and thereafter, part of the reactant, methyl 2,2-difluoro-3-hydroxy-4-methylpentanoate. Distillation was continued, obtaining 32.2 g (yield 33%, corrected yield 42% based on the consumed reactant with the recovered reactant being excluded) of 2,2,3,3,4,4,5,5-octafluoropentyl 2,2-difluoro-3-hydroxy-4-methylpentanoate, and 5.22 g (yield 8%) of methyl 2,2-difluoro-3-(2,2-difluoro-3-hydroxy-4-methylpentanoyloxy)-4-methylpentanoate.

2,2,3,3,4,4,5,5-octafluoropentyl
2,2-difluoro-3-hydroxy-4-methylpentanoate

Colorless Liquid
Boiling Point: 72° C./15 Pa
IR (D-ATR): ν=3486, 2975, 2887, 1785, 1402, 1286, 1205, 1175, 1131, 1061 cm$^{-1}$
$^1$H-NMR (600 MHz in DMSO-d$_6$): δ=0.93 (3H, d, J=6.9 Hz), 0.94 (3H, app dd, J=0.9, 6.9 Hz), 1.81-1.90 (1H, m), 3.58-3.72 (1H, m), 5.01 (1H, app q, J=13.8 Hz), 5.10 (1H, app q, J=13.8 Hz), 5.95 (1H, d, J=7.4 Hz, OH), 7.06 (1H, tt, J=5.5, 50 Hz) ppm
$^{13}$C-NMR (150 MHz in DMSO-d$_6$): δ=17.50, 19.33, 28.22, 60.63 (t, J=27 Hz), 73.73 (dd, J=22, 25 Hz), 107.90 (tt, J=30, 251 Hz), 108.1-112.4 (2C, m), 114.36 (tt, J=32, 256 Hz), 116.40 (dd, J=255, 259 Hz), 162.30 (dd, J=32, Hz) ppm
$^{19}$F-NMR (564 MHz in DMSO-d$_6$): δ=−139.82 (2F, d, J=49 Hz), −130.91 (2F, s), −125.92 (2F, s), −121.08 (1F, dd, J=19, 255 Hz), −120.28 (2F, s), −110.42 (1F, dd, J=8, 255 Hz) ppm methyl 2,2-difluoro-3-(2,2-difluoro-3-hydroxy-4-methylpentanoyloxy)-4-methylpentanoate This compound contains two asymmetric carbon atoms in the molecule and is available as a mixture of diastereomers.
Colorless Liquid
Boiling Point: 140° C./20 Pa
$^1$H-NMR (600 MHz in DMSO-d$_6$): δ=0.90-1.20 (12H, m), 1.84-1.92 (1H, m), 2.14-2.22 (1H, m), 3.58-3.68 (1H, m), 3.85 (3H, s), 5.30-5.41 (1H, m), 5.90 (1H, br. s, OH) ppm Example 11-2

Synthesis via alternative route of
2,2,3,3,4,4,5,5-octafluoropentyl
2,2-difluoro-3-hydroxy-4-methylpentanoate A catalytic amount of Amberlyst® (Rohm & Haas) was added to a mixture of 60.0 g of methyl 2,2-difluoro-3-hydroxy-4-methylpentanoate (synthesized in Example 9-1) and 300 g of 2,2,3,3,4,4,5,5-octafluoro-1-pentanol. With stirring in a nitrogen atmosphere, the mixture was heated under reflux for 42 hours while a fraction distilled below 65-90° C. was sequentially removed out of the system. After cooling, the reaction mixture was filtered and distilled in vacuum, recovering part of 2,2,3,3,4,4,5,5-octafluoro-1-pentanol and thereafter, part of the reactant, methyl 2,2-difluoro-3-hydroxy-4-methylpentanoate. Distillation was continued, obtaining 74.4 g (yield 66%, corrected yield 80% based on the consumed reactant with the recovered reactant being excluded) of 2,2,3,3,4,4,5,5-octafluoropentyl 2,2-difluoro-3-hydroxy-4-methylpentanoate. This compound had identical physical properties and spectra with those of Example 11-1.

Example 11-3

Synthesis of 2,2,3,3,4,4,5,5-octafluoropentyl
2,2-difluoro-3-methacryloyloxy-4-methylpentanoate
(Monomer 7)

With stirring at room temperature in a nitrogen atmosphere, a catalytic amount of methanesulfonic acid was added dropwise to a mixture of 20.45 g of 2,2,3,3,4,4,5,5-octafluoropentyl 2,2-difluoro-3-hydroxy-4-methylpentanoate, 10.4 g of methacrylic anhydride, and 100 g of toluene. The reaction mixture was stirred at 70° C. for 3 days. After cooling, the reaction mixture was poured into a saturated sodium hydrogen carbonate aqueous solution and extracted with ether. The ether solution was washed, dried, and concentrated. The residue was distilled in vacuum, obtaining 20.9 g (yield 87%) of the target compound, 2,2,3,3,4,4,5,5-octafluoropentyl 2,2-difluoro-3-methacryloyloxy-4-methylpentanoate (Monomer 7).

Monomer 7: 2,2,3,3,4,4,5,5-octafluoropentyl
2,2-difluoro-3-methacryloyloxy-4-methylpentanoate Colorless Liquid
Boiling Point: 77-79° C./20 Pa
IR (D-ATR): ν=2976, 1789, 1732, 1317, 1172, 1135, 1068 cm$^{-1}$
$^1$H-NMR (600 MHz in DMSO-d$_6$): δ=0.93 (3H, d, J=6.9 Hz), 0.96 (3H, d, J=6.9 Hz), 1.89 (3H, br. s), 2.12-2.20 (1H, m), 5.09 (1H, t, J=14.2 Hz), 5.22-5.28 (1H, m), 5.80 (1H, app s), 6.10 (1H, t, J=1.0 Hz), 7.06 (1H, tt, J=5.5, 50 Hz) ppm
$^{13}$C-NMR (150 MHz in DMSO-d$_6$): δ=16.91, 17.61, 19.10, 27.35, 61.33 (t, J=26 Hz), 73.94 (dd, J=23, 26 Hz), 107.86 (tt, J=30, 251 Hz), 113.79 (t, J=257 Hz), 107.70-116.20 (4C, m), 127.53, 134.52, 160.84 (app t, J=32 Hz), 165.11 ppm
$^{19}$F-NMR (564 MHz in DMSO-d$_6$): δ=−139.84 (2F, d, J=49 Hz), −130.86 (2F, s), −125.90 (2F, s), −120.40 (2F, app q, J=12 Hz), −114.28 (1F, dd, J=14, 263 Hz), −112.10 (1F, dd, J=11, 263 Hz) ppm Example 12

Synthesis of 3,3,4,4,5,5,6,6,6-nonafluorohexyl
2,2-difluoro-3-methacryloyloxy-4-methylpentanoate
(Monomer 8)

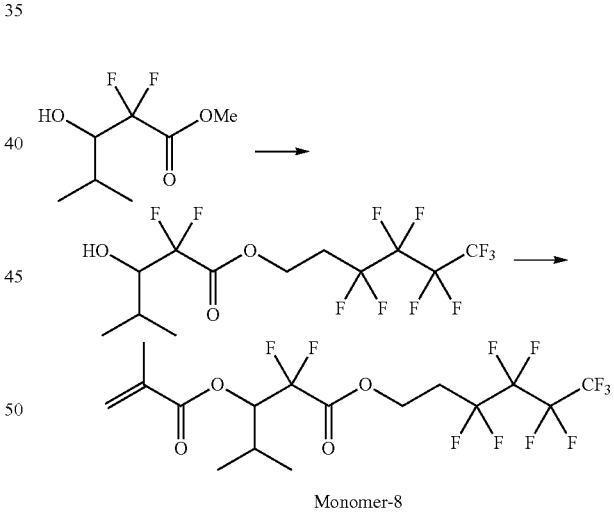

Monomer-8

Example 12-1

Synthesis of 3,3,4,4,5,5,6,6,6-nonafluorohexyl
2,2-difluoro-3-hydroxy-4-methylpentanoate The same procedure as Example 11 was repeated aside from using 3,3,4,4,5,5,6,6,6-nonafluorohexanol instead of 2,2,3,3,4,4,5,5-octafluoro-1-pentanol in Example 11-1, obtaining the target compound, 3,3,4,4,5,5,6,6,6-nonafluorohexyl 2,2-difluoro-3-hydroxy-4-methylpentanoate (yield 87%).

3,3,4,4,5,5,6,6,6-nonafluorohexyl 2,2-difluoro-3-hydroxy-4-methylpentanoate

Colorless Liquid
Boiling Point: 84° C./40 Pa
IR (D-ATR): ν=3498, 2974, 2885, 1770, 1474, 1222, 1135, 1060 cm$^{-1}$
$^1$H-NMR (600 MHz in DMSO-d$_6$): δ=0.91 (3H, d, J=6.4 Hz), 0.93 (3H, app dd, J=1.4, 6.9 Hz), 1.80-1.89 (1H, m), 2.67-2.82 (2H, m), 3.58-3.66 (1H, m), 4.48-4.58 (1H, m), 5.84 (1H, d, J=7.3 Hz, OH) ppm
$^{13}$C-NMR (150 MHz in DMSO-d$_6$): δ=17.41, 19.39 (d, J=2.9 Hz), 28.14, 29.16 (t, J=21 Hz), 58.36, 73.60 (app dd, J=22, Hz), 106.00-120.20 (4C, m), 116.24 (dd, J=254, 259 Hz), 163.19 (dd, J=31, 34 Hz) ppm
$^{19}$F-NMR (564 MHz in DMSO-d$_6$): δ=−127.14 (2F, dd, J=9.7, 14 Hz), −125.53 (2F, s), −114.50−−114.30 (2F, m), −121.39 (1F, dd, J=19, 254 Hz), −111.48 (1F, dd, J=8.7, 254 Hz), −82.07 (3F, app t, J=9 Hz) ppm

Example 12-2

The same procedure as Example 11 was repeated aside from using 3,3,4,4,5,5,6,6,6-nonafluorohexyl 2,2-difluoro-3-hydroxy-4-methylpentanoate instead of 2,2,3,3,4,4,5,5-octafluoropentyl 2,2-difluoro-3-hydroxy-4-methylpentanoate in Example 11-3, obtaining the target compound, 3,3,4,4,5,5,6,6,6-nonafluorohexyl 2,2-difluoro-3-methacryloyloxy-4-methylpentanoate (Monomer 8) in a yield of 44%.

3,3,4,4,5,5,6,6,6-nonafluorohexyl 2,2-difluoro-3-methacryloyloxy-4-methylpentanoate Colorless Liquid
Boiling Point: 93° C./40 Pa
IR (D-ATR): ν=2976, 2887, 1778, 1732, 1299, 1222, 1157, 1135, 1064 cm$^{-1}$
$^1$H-NMR (600 MHz in DMSO-d$_6$): δ=0.92 (3H, d, J=6.9 Hz), 0.94 (3H, d, J=6.9 Hz), 1.88 (3H, br. s), 2.11-2.19 (1H, m), 2.68-2.79 (2H, m), 4.50-4.59 (2H, m), 5.19-5.26 (1H, m), 5.78 (1H, app s), 6.09 (1H, app s) ppm
$^{13}$C-NMR (150 MHz in DMSO-d$_6$): δ=16.82, 17.59, 19.10, 27.26, 29.02 (t, J=22 Hz), 59.21, 74.01 (dd, J=23, 26 Hz), 113.70 (app t, J=256 Hz), 106.00-120.20 (4C, m), 127.38, 134.62, 161.74 (app t, J=32 Hz), 165.20 ppm
$^{19}$F-NMR (564 MHz in DMSO-d$_6$): δ=−127.13 (2F, dd, J=10, 14 Hz), −125.70−−125.40 (2F, m), −114.84 (1F, dd, J=14, 261 Hz), −114.55−−114.35 (2F, m), −113.18 (1F, dd, J=11, 261 Hz), −82.03 (3F, app t, J=9 Hz) ppm

Example 13

Synthesis of methyl 2,2-difluoro-3-(2,2-difluoro-3-methacryloyloxy-4-methylpentanoyloxy)-4-methylpentanoate (Monomer 9)

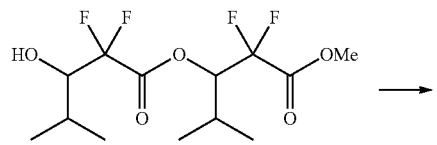

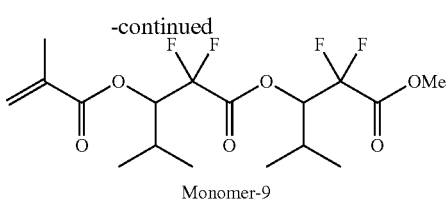

Monomer-9

Reaction was conducted by the same procedure as Example 11 aside from using methyl 2,2-difluoro-3-(2,2-difluoro-3-hydroxy-4-methylpentanoyloxy)-4-methylpentanoate in Example 11-1 instead of 2,2,3,3,4,4,5,5-octafluoropentyl 2,2-difluoro-3-hydroxy-4-methylpentanoate in Example 11-3. Subsequent purification was conducted by silica gel column chromatography instead of vacuum distillation. The target compound, methyl 2,2-difluoro-3-(2,2-difluoro-3-methacryloyloxy-4-methylpentanoyloxy)-4-methylpentanoate was obtained in a yield of 49%.

Monomer 9: methyl 2,2-difluoro-3-(2,2-difluoro-3-methacryloyloxy-4-methylpentanoyloxy)-4-methylpentanoate This compound contains two asymmetric carbon atoms in the molecule and is available as a mixture of diastereomers.
Colorless Liquid
Boiling Point: 140° C./20 Pa
IR (D-ATR): ν=2974, 2888, 1780, 1733, 1317, 1294, 1224, 1154, 1059 cm$^{-1}$
$^1$H-NMR (600 MHz in DMSO-d$_6$): δ=0.89-1.00 (12H, m), 1.88 (3H, br. s), 2.11-2.22 (2H, m), 3.86 (3H, s), 5.24-5.33 (1H, m), 5.36-5.44 (1H, m), 5.77-5.82 (1H, m), 6.09 (1H, app s) ppm
$^{13}$C-NMR (150 MHz in DMSO-d$_6$): δ=16.43, 16.47, 16.98, 17.08, 17.64, 18.68, 18.73, 19.14, 27.18, 27.53, 54.25, 73.50-74.00 (m), 76.60-77.36 (m), 112.88 (app t, J=256 Hz), 112.98 (app t, J=256 Hz), 113.98 (dd, J=256, 257 Hz), 113.98 (dd, J=254, 259 Hz), 114.30 (dd, J=254, 259 Hz), 127.46, 127.66, 134.54, 134.57, 161.24 (app t, J=32 Hz), 161.35 (app t, J=32 Hz), 161.98 (app t, J=32 Hz), 164.93, 165.09 ppm. Since peaks assigned to diastereomers are in part separately observed, the number of peaks does not correspond to the carbon count computed from the planar formula.

Example 14

Synthesis of methyl 2,2-difluoro-3-methacryloyloxyhexanoate (Monomer 10)

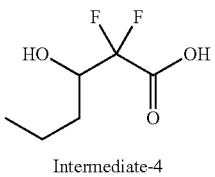

Intermediate-4

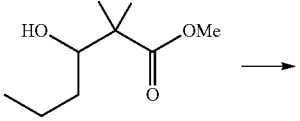

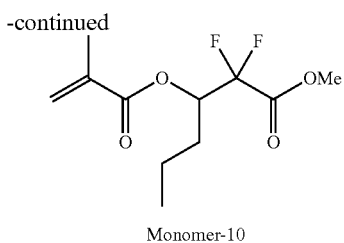

Monomer-10

Example 14-1

Synthesis of methyl 2,2-difluoro-3-hydroxyhexanoate

A catalytic amount of p-toluenesulfonic acid monohydrate was added to a mixture of 75.5 g of Intermediate 4 in Example 4 and 200 g of methanol. With stirring in a nitrogen atmosphere, the reaction mixture was heated under reflux for 10 hours. After cooling, the reaction mixture was poured into a saturated sodium hydrogen carbonate aqueous solution and extracted with ethyl acetate. The ethyl acetate solution was washed, dried and concentrated, obtaining 63.0 g (yield 58%) of methyl 2,2-difluoro-3-hydroxyhexanoate. This crude product had a sufficient purity as an intermediate and was ready for use in the subsequent step.

methyl 2,2-difluoro-3-hydroxyhexanoate

Yellow Liquid

IR (D-ATR): ν=3472, 2964, 2878, 1763, 1443, 1319, 1213, 1114, 1080, 1061 cm$^{-1}$ $^1$H-NMR (600 MHz in DMSO-d$_6$): δ=0.88 (3H, t, J=7.1 Hz), 1.28-1.54 (4H, m), 3.82 (3H, s), 3.81-3.89 (1H, m), 5.80 (1H, br., OH) ppm $^{13}$C-NMR (150 MHz in DMSO-d$_6$): δ=13.57, 17.94, 30.65 (d, J=3 Hz), 53.34, 69.54 (dd, J=24, 27 Hz), 115.66 (dd, J=252, 256 Hz), 163.87 (app t, J=32 Hz) ppm $^{19}$F-NMR (564 MHz in DMSO-d$_6$): δ=−121.74 (1F, dd, J=17, 253 Hz), −112.76 (1F, dd, J=8, 253 Hz) ppm

Example 14-2

Synthesis of methyl 2,2-difluoro-3-methacryloyloxyhexanoate (Monomer 10)

With stirring at room temperature in a nitrogen atmosphere, 28.4 g of triethylamine was added dropwise to a mixture of 30.06 g of methyl 2,2-difluoro-3-hydroxyhexanoate, 28.4 g of methacryloyl chloride, and 300 ml of acetonitrile. The reaction mixture was stirred overnight at room temperature. Thereafter, 30 ml of water and 20 ml of triethylamine were added to the reaction mixture, which was stirred for a further 1 hour at room temperature. The reaction mixture was poured into water and extracted with ethyl acetate. The solution was washed, dried, and concentrated. The residue was distilled in vacuum, obtaining 21.54 g (yield 52%) of the target compound, methyl 2,2-difluoro-3-methacryloyloxyhexanoate (Monomer 10).

Monomer 10: methyl 2,2-difluoro-3-methacryloyloxyhexanoate

Colorless Liquid

Boiling Point: 62-63° C./80 Pa

IR (D-ATR): ν=2965, 2937, 2878, 1771, 1731, 1441, 1316, 1153, 1110, 1059 cm$^{-1}$ $^1$H-NMR (600 MHz in DMSO-d$_6$): δ=0.88 (3H, t, J=7.3 Hz), 1.21-1.38 (2H, m), 1.62-1.73 (2H, m), 1.88 (3H, br. s), 5.34-5.42 (1H, m), 5.78 (1H, app t, J=1.4 Hz), 6.07 (1H, br. s) ppm $^{13}$C-NMR (150 MHz in DMSO-d$_6$): δ=13.25, 17.58, 17.70, 28.78, 53.99, 70.62 (dd, J=25, 27 Hz), 113.37 (t, J=255 Hz), 127.42, 134.63, 162.40 (t, J=31 Hz), 165.27 ppm $^{19}$F-NMR (564 MHz in DMSO-d$_6$): δ=−117.75 (1F, dd, J=13, 259 Hz), −115.35 (1F, dd, J=10, 259 Hz) ppm

Example 15

Synthesis of methyl 2,2-difluoro-3-methacryloyloxy-3-methylbutanoate (Monomer 11)

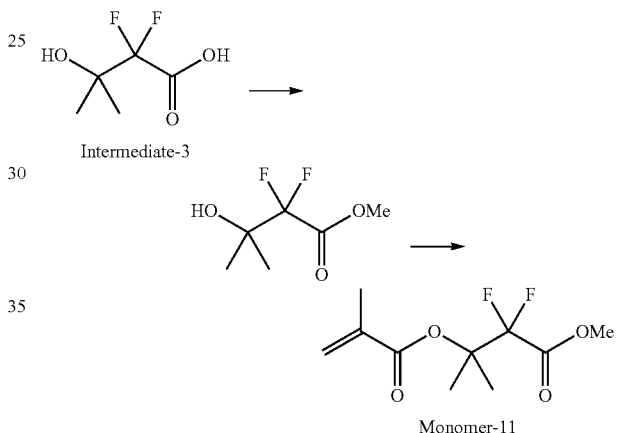

Example 15-1

Synthesis of methyl 2,2-difluoro-3-hydroxy-3-methylbutanoate

A catalytic amount of p-toluenesulfonic acid monohydrate was added to a mixture of 73.3 g of Intermediate 3 in Example 3 and 300 g of methanol. With stirring in a nitrogen atmosphere, the reaction mixture was heated under reflux for 12 hours. After cooling, the reaction mixture was poured into a saturated sodium hydrogen carbonate aqueous solution and extracted with ethyl acetate. The ethyl acetate solution was washed, dried and concentrated. The residue was distilled in vacuum, obtaining 52.0 g (yield 65%) of methyl 2,2-difluoro-3-hydroxy-3-methylbutanoate.

methyl 2,2-difluoro-3-hydroxy-3-methylbutanoate

Yellow Liquid

IR (D-ATR): ν=3502, 2995, 2961, 1766, 1442, 1315, 1195, 1116, 1062 cm$^{-1}$ $^1$H-NMR (600 MHz in DMSO-d$_6$): δ=1.22 (6H, s), 3.80 (3H, s), 5.57 (1H, s, OH) ppm $^{13}$C-NMR (150 MHz in DMSO-d$_6$): δ=23.28 (2C), 53.21, 71.12 (t, J=25 Hz), 116.81 (t, J=258 Hz), 163.73 (t, J=33 Hz) ppm $^{19}$F-NMR (564 MHz in DMSO-d$_6$): δ=−117.38 (2F) ppm

Example 15-2

Synthesis of methyl 2,2-difluoro-3-methacryloyloxy-3-methylbutanoate (Monomer 11)

With stirring at room temperature in a nitrogen atmosphere, 72.6 g of triethylamine was added dropwise to a mixture of 30.0 g of methyl 2,2-difluoro-3-hydroxy-3-methylbutanoate, 30.0 g of methacryloyl chloride, and 250 ml of acetonitrile. The reaction mixture was stirred overnight at room temperature. Thereafter, 30 ml of water and a catalytic amount of 4-dimethylaminopyridine were added to the reaction mixture, which was stirred for a further 1 hour at room temperature. The reaction mixture was poured into water and extracted with ethyl acetate. The solution was washed, dried, and concentrated. The residue was distilled in vacuum, obtaining 36.72 g (yield 88%) of the target compound, methyl 2,2-difluoro-3-methacryloyloxy-3-methylbutanoate (Monomer 11).

Monomer 11: methyl 2,2-difluoro-3-methacryloyloxy-3-methylbutanoate

Colorless Liquid
Boiling Point: 42° C./27 Pa
IR (D-ATR): ν=3000, 2960, 1769, 1727, 1440, 1318, 1303, 1159, 1135, 1064 cm$^{-1}$
$^1$H-NMR (600 MHz in DMSO-d$_6$): δ=1.63 (6H, s), 1.81 (3H, s), 3.87 (3H, s), 5.68-5.72 (1H, m), 5.96 (1H, app s) ppm
$^{13}$C-NMR (150 MHz in DMSO-d$_6$): δ=17.61 (2C), 19.24, 53.81, 81.21 (t, J=26 Hz), 114.31 (t, J=258 Hz), 126.58, 136.08, 162.48 (t, J=32 Hz), 164.47 ppm
$^{19}$F-NMR (564 MHz in DMSO-d$_6$): δ=−118.39 (2F) ppm

Example 16

Synthesis of 2,2,3,3,4,4,5,5-octafluoropentyl 2,2-difluoro-3-methacryloyloxy-5-methylhexanoate (Monomer 12)

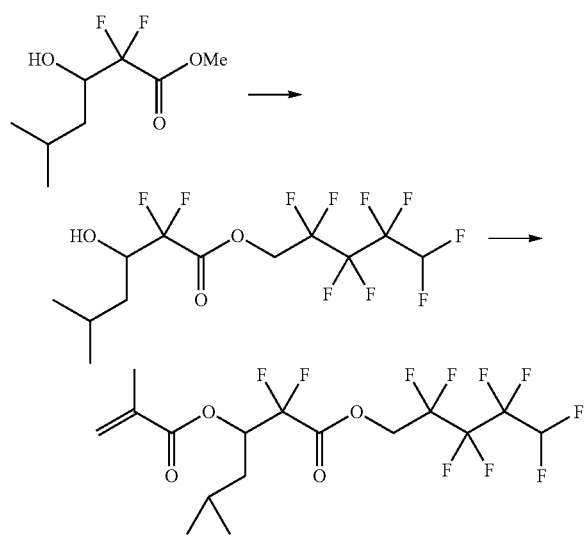

Monomer-12

Example 16-1

Synthesis of 2,2,3,3,4,4,5,5-octafluoropentyl 2,2-difluoro-3-hydroxy-5-methylhexanoate A catalytic amount of potassium t-butoxide was added to a mixture of 55.86 g of methyl 2,2-difluoro-3-hydroxy-5-methylhexanoate in Example 5-1 and 75 g of 2,2,3,3,4,4,5,5-octafluoro-1-pentanol. With stirring in a nitrogen atmosphere, the reaction mixture was heated under reflux for 48 hours while a fraction distilled below 100-115° C. was sequentially removed out of the system. After cooling, the reaction mixture was distilled in vacuum, recovering part of 2,2,3,3,4,4,5,5-octafluoro-1-pentanol and then part of the reactant, methyl 2,2-difluoro-3-hydroxy-5-methylhexanoate. Distillation was further continued, obtaining 31.15 g (yield 28%, corrected yield 36% based on the consumed reactant with the recovered reactant being excluded) of 2,2,3,3,4,4,5,5-octafluoropentyl 2,2-difluoro-3-hydroxy-5-methylhexanoate.

2,2,3,3,4,4,5,5-octafluoropentyl 2,2-difluoro-3-hydroxy-5-methylhexanoate

Yellow Liquid
Boiling Point: 96° C./150 Pa
IR (D-ATR): ν=3449, 2965, 2877, 1784, 1311, 1291, 1174, 1132, 1076 cm$^{-1}$
$^1$H-NMR (600 MHz in DMSO-d$_6$): δ=0.85 (3H, d, J=6.4 Hz), 0.91 (3H, d, J=6.9 Hz), 1.17-1.24 (1H, m), 1.43-1.51 (1H, m), 1.74-1.83 (1H, m), 3.87-4.01 (1H, m), 4.99-5.17 (2H, m), 5.92 (1H, br. d, J=6 Hz, OH), 7.06 (1H, tt, J=6, 50 Hz) ppm
$^{13}$C-NMR (150 MHz in DMSO-d$_6$): δ=20.81, 23.32, 23.39, 37.23, 60.69 (t, J=27 Hz), 68.23 (t, J=25 Hz), 106.00-117.50 (5C, m), 162.08 (t, J=34 Hz) ppm
$^{19}$F-NMR (564 MHz in DMSO-d$_6$): δ=−139.83 (2F, d, J=50 Hz), −131.00−−130.80 (2F, m), −125.90 (2F, t, J=8 Hz), −121.83 (1F, dd, J=16, 254 Hz), −120.35−−120.10 (2F, m), −115.15 (1F, dd, J=9, 254 Hz) ppm

Example 16-2

Synthesis of 2,2,3,3,4,4,5,5-octafluoropentyl 2,2-difluoro-3-methacryloyloxy-5-methylhexanoate (Monomer 12)

With stirring at room temperature in a nitrogen atmosphere, a catalytic amount of methanesulfonic acid was added dropwise to a mixture of 21.83 g of 2,2,3,3,4,4,5,5-octafluoropentyl 2,2-difluoro-3-hydroxy-5-methylhexanoate, 11.7 g of methacrylic anhydride, and 100 ml of toluene. The reaction mixture was stirred for 2 days at 70° C. After cooling, the reaction mixture was diluted with ether and poured into a saturated sodium hydrogen carbonate aqueous solution. A catalytic amount of 4-dimethylaminopyridine was added to the solution, which was stirred overnight at room temperature. The organic layer was washed, dried, and concentrated. The residue was distilled in vacuum, obtaining 25.3 g (yield 99%) of the target compound, 2,2,3,3,4,4,5,5-octafluoropentyl 2,2-difluoro-3-methacryloyloxy-5-methylhexanoate (Monomer 12).

Monomer 12: 2,2,3,3,4,4,5,5-octafluoropentyl 2,2-difluoro-3-methacryloyloxy-5-methylhexanoate Colorless Liquid
Boiling Point: 82° C./11 Pa
IR (D-ATR): ν=2966, 1790, 1732, 1313, 1294, 1173, 1157, 1131 cm$^{-1}$
$^{1}$H-NMR (600 MHz in DMSO-d$_{6}$): δ=0.87 (3H, d, J=6.9 Hz), 0.89 (3H, d, J=6.4 Hz), 1.45-1.52 (1H, m), 1.52-1.61 (1H, m), 1.65-1.73 (1H, m), 1.87 (3H, br. s), 5.04-5.16 (1H, m), 5.44-5.52 (1H, m), 5.78 (1H, app t, J=2 Hz), 6.08 (1H, app s), 7.04 (1H, tt, J=5.5, 50 Hz) ppm
$^{13}$C-NMR (150 MHz in DMSO-d$_{6}$): δ=17.56, 20.56, 22.74, 23.59, 61.32 (t, J=26 Hz), 69.23 (t, J=25 Hz), 107.89 (tt, J=31, 251 Hz), 110.27 (tt, J=31, 264 Hz), 110.48 (tt, J=31, 265 Hz), 113.37 (t, J=256 Hz), 114.24 (tt, J=31, 257 Hz), 127.53, 134.53, 160.59 (t, J=32 Hz), 165.20 ppm
$^{19}$F-NMR (564 MHz in DMSO-d$_{6}$): δ=−139.93 (2F, d, J=50 Hz), −130.94 (2F, d, J=4.4 Hz), −125.99 (2F, t, J=7.6 Hz), −120.46 (2F, app q, J=12 Hz), −116.57 (1F, dd, J=11, 261 Hz), −115.51 (1F, dd, J=11, 261 Hz) ppm Example 17

Synthesis of methyl 2,2-difluoro-3-methacryloyloxy-acetoxy-4-methylpentanoate (Monomer 13)

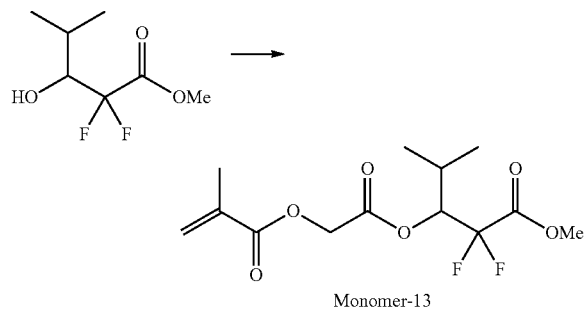

Monomer-13

With stirring at room temperature in a nitrogen atmosphere, 18.86 g of methyl 2,2-difluoro-3-hydroxy-4-methylpentanoate in Example 9-1 was added dropwise to a mixture of 22.6 g of methacryloyloxyacetyl chloride and 100 ml of toluene, and then 13.8 g of pyridine added. The reaction mixture was stirred overnight at room temperature, poured into a saturated sodium hydrogen carbonate aqueous solution, and extracted with ethyl acetate. The ethyl acetate solution was washed, dried, and concentrated. The residue was distilled in vacuum, obtaining 29.80 g (yield 93%) of the target compound, methyl 2,2-difluoro-3-methacryloyloxyacetoxy-4-methylpentanoate (Monomer 13).

Monomer 13: methyl 2,2-difluoro-3-methacryloyloxyacetoxy-4-methylpentanoate

Colorless Liquid
Boiling Point: 99° C./20 Pa
IR (D-ATR): ν=2971, 1778, 1731, 1441, 1322, 1203, 1150, 1062 cm$^{-1}$
$^{1}$H-NMR (600 MHz in DMSO-d$_{6}$): δ=0.91 (3H, d, J=6.9 Hz), 0.95 (3H, d, J=6.9 Hz), 1.91 (3H, s), 2.06-2.15 (1H, m), 3.86 (3H, s), 4.84 (1H, d, J=16 Hz), 4.90 (1H, d, J=16 Hz), 5.20-5.27 (1H, m), 5.77-5.81 (1H, m), 6.12 (1H, br. s) ppm $^{13}$C-NMR (150 MHz in DMSO-d$_{6}$): δ=16.83, 17.74, 18.99, 27.23, 54.13, 60.52, 74.39 (dd, J=23, 27 Hz), 113.53 (t, J=256 Hz), 127.10, 134.86, 162.37 (t, J=31 Hz), 165.99, 166.91 ppm
$^{19}$F-NMR (564 MHz in DMSO-d$_{6}$): δ=−115.00 (1F, dd, J=15, 262 Hz), −112.88 (1F, dd, J=12, 262 Hz) ppm Example 18

Synthesis of methyl 2,2-difluoro-3-methacryloyloxy-acetoxy-5-methylhexanoate (Monomer 14)

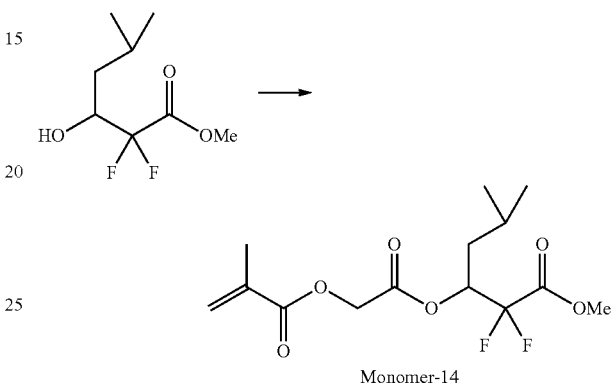

Monomer-14

The same procedure as Example 17 was repeated aside from using methyl 2,2-difluoro-3-hydroxy-5-methylhexanoate in Example 5-1 instead of methyl 2,2-difluoro-3-hydroxy-4-methylpentanoate in Example 17, obtaining the target compound, methyl 2,2-difluoro-3-methacryloyloxyacetoxy-5-methylhexanoate (Monomer 14) in a yield of 53%.

Monomer 14: methyl 2,2-difluoro-3-methacryloyloxyacetoxy-5-methylhexanoate

Colorless Liquid
Boiling Point: 101° C./13 Pa
IR (D-ATR): ν=2962, 1778, 1731, 1441, 1320, 1202, 1150, 1068 cm$^{-1}$
$^{1}$H-NMR (600 MHz in DMSO-d$_{6}$): δ=0.86 (3H, d, J=6.9 Hz), 0.90 (3H, d, J=6.4 Hz), 1.40-1.47 (1H, m), 1.56-1.47 (1H, m), 1.90 (3H, t), 3.86 (3H, s), 4.81 (1H, d, J=16 Hz), 4.87 (1H, d, J=16 Hz), 5.38-5.47 (1H, m), 5.78-5.80 (1H, m), 6.11 (1H, t, J=1 Hz) ppm
$^{13}$C-NMR (150 MHz in DMSO-d$_{6}$): δ=17.76, 20.82, 22.93, 23.17, 35.34, 54.16, 60.54, 69.57 (dd, J=24, 28 Hz), 113.03 (t, J=255 Hz), 127.09, 134.84, 162.10 (t, J=32 Hz), 165.94, 166.93 ppm
$^{19}$F-NMR (564 MHz in DMSO-d$_{6}$): δ=−117.69 (1F, dd, J=13, 261 Hz), −115.62 (1F, dd, J=11, 261 Hz) ppm Example 19

Polymers were synthesized according to the following formulation.

Example 19-1

Synthesis of Polymer 1

In a nitrogen blanket, a flask was charged with 8.96 g of Monomer 1, 6.41 g of 4,4,4-trifluoro-3-hydroxy-2-methyl-3- trifluoromethylbutan-2-yl methacrylate, 0.63 g of dimethyl 2,2'-azobis(isobutyrate), and 15 g of methyl ethyl ketone to form a monomer solution which was kept at 20-25° C. In a nitrogen blanket, another flask was charged with 7.5 g of methyl ethyl ketone, which was heated under reflux with stirring. The monomer solution was added dropwise thereto over 4 hours. After the completion of dropwise addition, the solution was stirred for a further 2 hours for polymerization while maintaining the solution under the reflux condition. At the end of maturing, the solution was cooled to room temperature and added dropwise to 150 g of hexane whereupon a copolymer precipitated. The copolymer was collected by filtration, washed with 90 g of hexane, and separated as a white solid. The white solid was vacuum dried at 50° C. for 20 hours, yielding the target polymer, designated Polymer 1, in white powder solid form. Amount 10.3 g, yield 64%.

Polymer 1

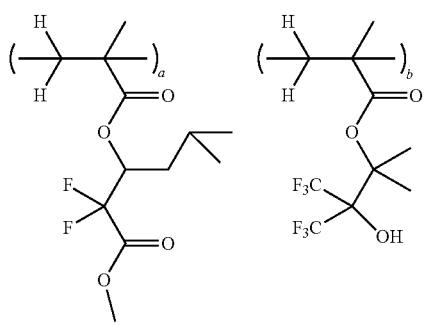

(a = 0.60, b = 0.40, Mw = 5,800)

Examples 19-2 to 19-12

Synthesis of Polymers 2 to 12

Polymers were synthesized by the same procedure as in Synthesis Example 19-1, aside from changing the type and amount of monomers. It is noted that the values of a and b are molar ratios of monomer units.

Polymer 2

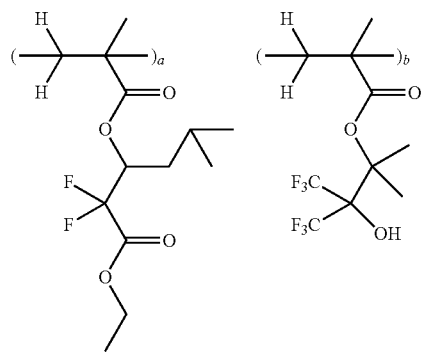

(a = 0.60, b = 0.40, Mw = 7,500)

-continued

Polymer 3

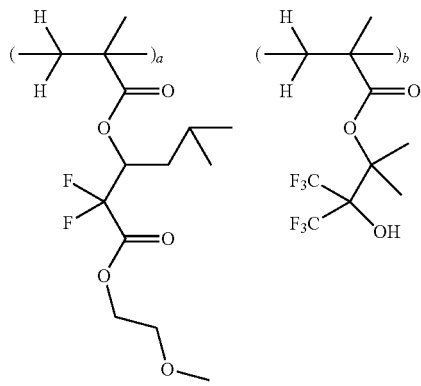

(a = 0.60, b = 0.40, Mw = 6,600)

Polymer 4

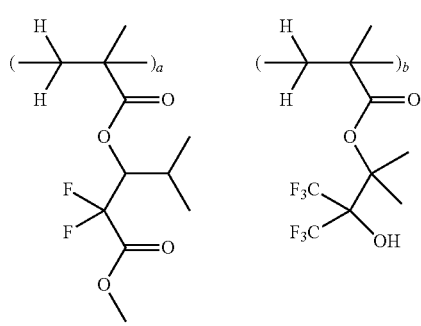

(a = 0.60, b = 0.40, Mw = 5,500)

Polymer 5

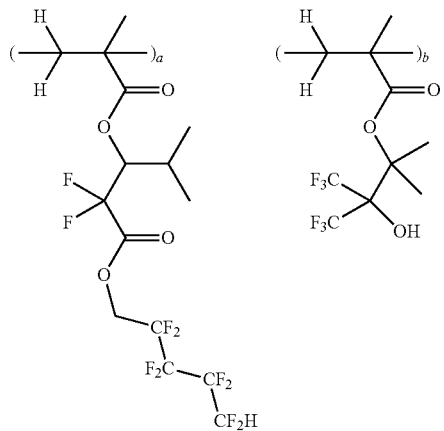

(a = 0.60, b = 0.40, Mw = 6,100)

Polymer 6
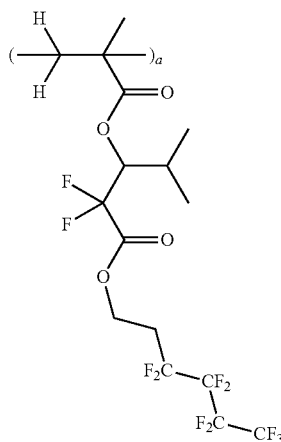 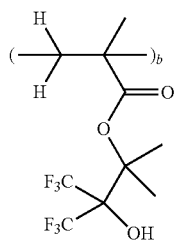
(a = 0.60, b = 0.40, Mw = 7,600)
Polymer 7
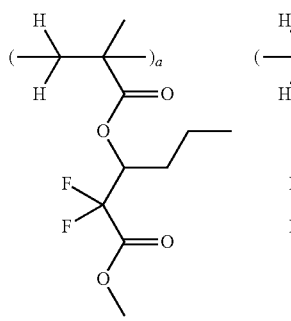 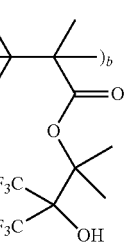
(a = 0.60, b = 0.40, Mw = 7,800)
Polymer 8
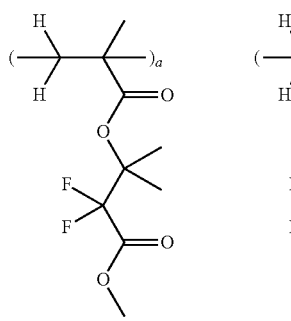
(a = 0.60, b = 0.40, Mw = 8,700)
Polymer 9
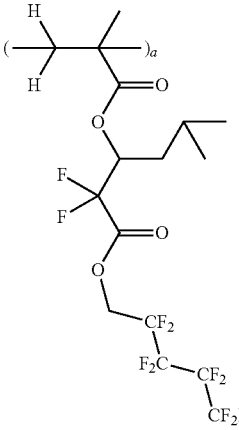 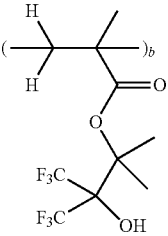
(a = 0.60, b = 0.40, Mw = 9,300)
Polymer 10
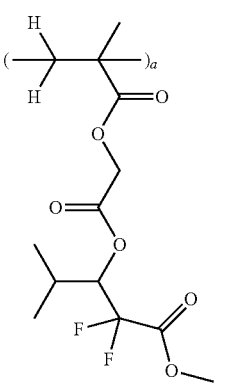
(a = 0.60, b = 0.40, Mw = 10,800)
Polymer 11
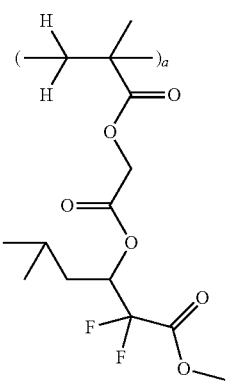
(a = 0.60, b = 0.40, Mw = 11,500)
Polymer 12
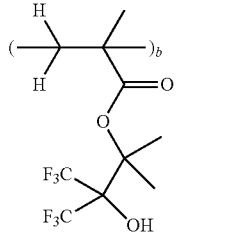
(b = 1.00, Mw = 8,700)

Examples 20-1 to 20-11 & Comparative Examples 1-1 and 1-2

Evaluation of Resist

A resist solution was prepared by dissolving 5 g of Resist Polymer (shown below), 0.25 g of an additive polymer selected from Polymers 1 to 12, 0.25 g of PAG1 (shown below), and 0.05 g of Quencher 1 (shown below) in 75 g of propylene glycol monomethyl ether acetate (PGMEA) and filtering through a polypropylene filter having a pore size of 0.2 μm. In Comparative Example 1-2, a resist solution was similarly prepared aside from omitting the additive polymer.

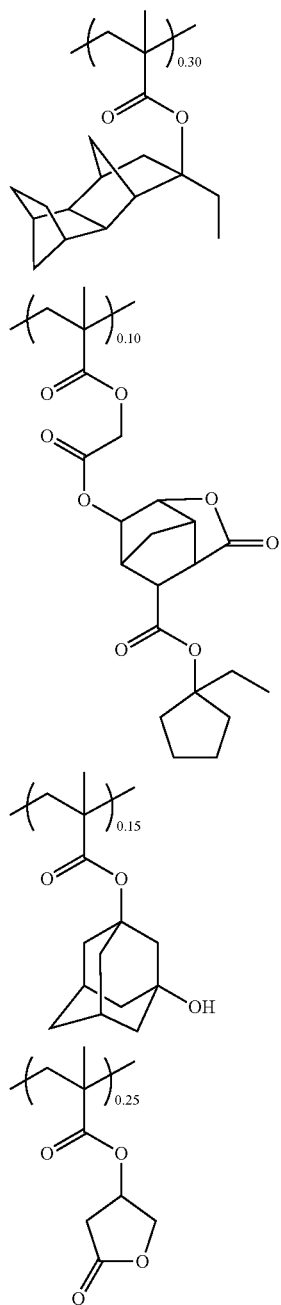

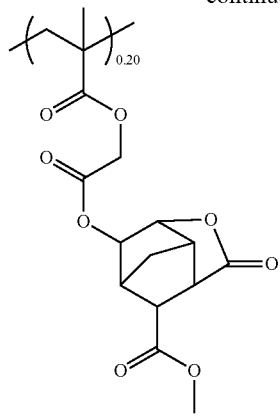

Resist Polymer
Mw = 7,600; Mw/Mn = 1.6

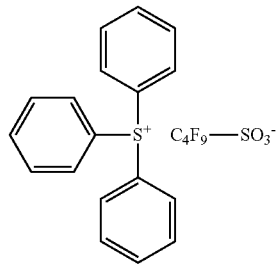

PAG 1

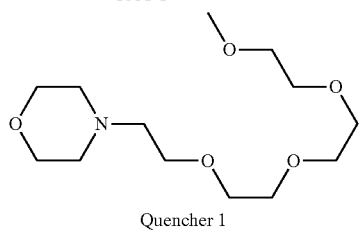

Quencher 1

An antireflective coating ARC-29A (Nissan Chemical Industries, Ltd.) was deposited on a silicon substrate to a thickness of 87 nm. The resist solution was applied onto the ARC and baked at 90° C. for 60 seconds to form a resist film of 90 nm thick.

A contact angle with water of the resist film was measured, using an inclination contact angle meter Drop Master 500 by Kyowa Interface Science Co., Ltd. Specifically, the wafer covered with the resist film was kept horizontal, and 50 μL of pure water was dropped on the resist film to form a droplet. While the wafer was gradually inclined, the angle (sliding angle) at which the droplet started sliding down was determined as well as receding contact angle. The results are shown in Table 1.

Also, the resist film-bearing wafer (prepared above) was irradiated through an open frame at an energy dose of 50 mJ/cm$^2$ using an ArF scanner S305B (Nikon Corp.). Then a true circle ring of Teflon® having an inner diameter of 10 cm was placed on the resist film, 10 mL of pure water was carefully injected inside the ring, and the resist film was kept in contact with water at room temperature for 60 seconds. Thereafter, the water was recovered, and a concentration of photoacid generator (PAG1) anion in the water was measured by an LC-MS analyzer (Agilent). The results are also shown in Table 1.

Further, the resist film-bearing wafer (prepared above) was exposed by means of an ArF scanner model S307E (Nikon Corp., NA 0.85, σ 0.93, 4/5 annular illumination, 6% halftone phase shift mask), rinsed for 5 minutes while splashing pure water, baked (PEB) at 110° C. for 60 seconds, and developed with a 2.38 wt % tetramethylammonium hydroxide aqueous solution for 60 seconds, forming a 75-nm line-and-space pattern. The wafer was sectioned, and the profile and sensitivity of the 75-nm line-and-space pattern were evaluated. The results are also shown in Table 1.

TABLE 1

| | | Additive polymer | Sliding angle (°) | Receding contact angle (°) | Anion leach-out (ppb) | Sensitivity (mJ/cm$^2$) | 75-nm pattern profile | Contact angle with water after development (°) |
|---|---|---|---|---|---|---|---|---|
| Example | 20-1 | Polymer 1 | 15 | 69 | 8 | 31 | rectangular | 42 |
| | 20-2 | Polymer 2 | 12 | 74 | 7 | 31 | rectangular | 52 |
| | 20-3 | Polymer 3 | 16 | 65 | 8 | 31 | rectangular | 42 |
| | 20-4 | Polymer 4 | 17 | 62 | 8 | 31 | rectangular | 38 |
| | 20-5 | Polymer 5 | 16 | 73 | 7 | 31 | rectangular | 31 |
| | 20-6 | Polymer 6 | 18 | 77 | 6 | 31 | rectangular | 40 |
| | 20-7 | Polymer 7 | 16 | 66 | 8 | 31 | rectangular | 39 |
| | 20-8 | Polymer 8 | 13 | 67 | 8 | 31 | rectangular | 42 |
| | 20-9 | Polymer 9 | 13 | 80 | 6 | 31 | rectangular | 30 |
| | 20-10 | Polymer 10 | 14 | 67 | 8 | 32 | rectangular | 36 |
| | 20-11 | Polymer 11 | 13 | 72 | 7 | 31 | rectangular | 39 |
| Comparative | 1-1 | Polymer 12 | 20 | 56 | 5 | 33 | rectangular | 37 |
| Example | 1-2 | — | 28 | 39 | 60 | 31 | T-top | 75 |

A smaller sliding angle indicates an easier flow of water on the resist film. A larger receding contact angle indicates that fewer liquid droplets are left during high-speed scan exposure. A resist film having a smaller sliding angle and a larger receding contact angle is desirable. It is demonstrated in Table 1 that the inclusion of the additive polymer of the invention in a resist solution achieves a drastic improvement in the receding contact angle of resist film without adversely affecting the sliding angle, as compared with the resist film free of the additive polymer.

Also, a comparison among Examples 20-1, 20-7 and 20-8 reveals that the resist films using Polymers 1 and 8 having branched alkyl show a smaller sliding angle and a larger receding contact angle. The resist films using Polymers 5, 6 and 9 having fluoroalkyl and branched alkyl show a dramatically increased receding contact angle.

If part of the acid generated in the resist film or the basic compound added to the resist material is leached in water, there is a possibility that the pattern eventually changes its profile or collapses. It is evident from Table 1 that a resist film formed from a resist solution containing the additive polymer of the invention is effective in inhibiting the PAG from being leached out of the film in water.

As seen from Table 1, when exposure is followed by water rinsing, the resist film having the additive polymer of the invention formulated therein formed a pattern of rectangular profile, in stark contrast with the resist film free of the additive polymer forming a pattern of T-top profile.

A large contact angle with water after development indicates a likelihood of defects known as "blob defects" forming in a resist film. An improvement in alkaline hydrolysis leads to a small contact angle with water after development and hence, a less likelihood of blob defect formation. A comparison between Examples 20-1 and 20-11 and between Examples 20-4 and 20-10 in Table 1 reveals that Polymers 11 and 10 wherein k=1 in formula (1a) provide a small contact angle with water after development as compared with Polymers 1 and 4 wherein k=0. It is thus concluded that a polymer having more hydrolysis sites as in the case of k=1 is improved in alkaline dissolution and minimized in blob defects.

Japanese Patent Application No. 2010-225358 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising:

recurring units having the general formula (1a)

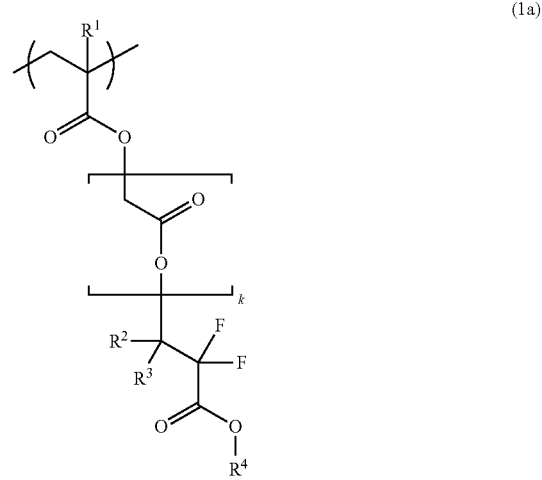

(1a)

wherein $R^1$ is hydrogen, methyl or trifluoromethyl, $R^2$ and $R^3$ are each independently hydrogen or a straight, branched or cyclic monovalent $C_1$-$C_{20}$ hydrocarbon group, or $R^2$ and $R^3$ taken together represent a divalent group which forms a $C_3$-$C_{20}$ hydrocarbon ring with the carbon atom to which they are attached, $R^4$ is a group having the general formula (A):

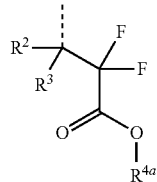
(A)

wherein $R^2$ and $R^3$ are as defined above, $R^{4a}$ is a primary $C_1$-$C_5$ alkyl group, a $C_2$-$C_8$ fluoroalkyl group or a group: MeO(CH$_2$CH$_2$O)$_n$CH$_2$CH$_2$— or EtO(CH$_2$CH$_2$O)$_n$CH$_2$CH$_2$— wherein Me is methyl, Et is ethyl, and n is 0, 1 or 2, and the broken line denotes a valence bond, and k is 0 or 1; and recurring units having the following formula (i) or (ii)

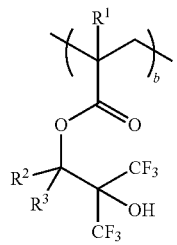
(i)

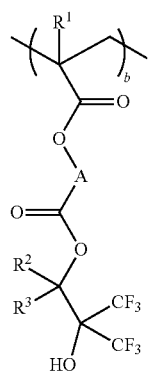
(ii)

wherein $R^1$, $R^2$, and $R^3$ are as defined above, A is a straight, branched or cyclic $C_1$-$C_6$ alkylene group, and b is a number in the range: $0 \leq b < 1.0$.

2. A polymer comprising recurring units having the general formula (1a):

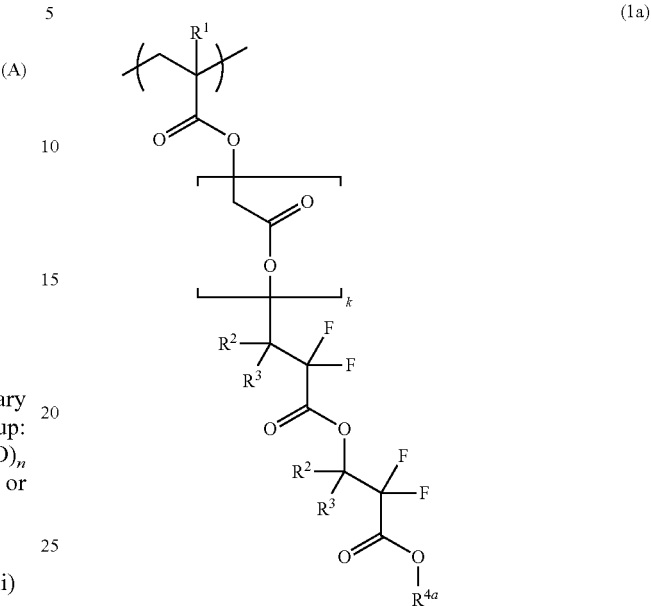
(1a)

wherein $R^1$ is hydrogen, methyl or trifluoromethyl, $R^2$ and $R^3$ are each independently hydrogen or a straight, branched or cyclic monovalent $C_1$-$C_{20}$ hydrocarbon group, or $R^2$ and $R^3$ taken together represent a divalent group which forms a $C_3$-$C_{20}$ hydrocarbon ring with the carbon atom to which they are attached, $R^{4a}$ is a primary $C_1$-$C_5$ alkyl group, a $C_2$-$C_8$ fluoroalkyl group or a group of the formula: MeO(CH$_2$CH$_2$O)$_n$CH$_2$CH$_2$— or EtO(CH$_2$CH$_2$O)$_n$CH$_2$CH$_2$— wherein Me is methyl, Et is ethyl, n is 0, 1 or 2, and k is 0 or 1.

3. The polymer of claim 2, which further comprises recurring units of at least one type selected from the following general formulae (10a) to (10i):

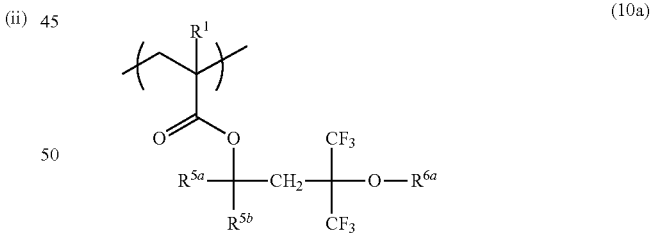
(10a)

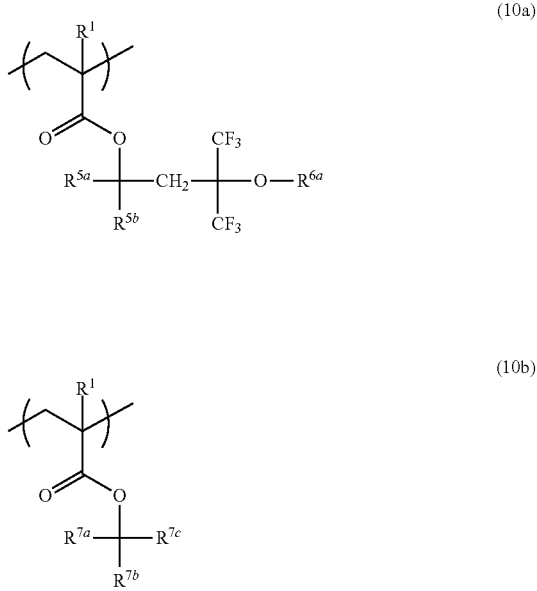
(10b)

-continued (10c) 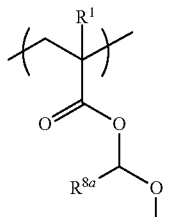

(10d) 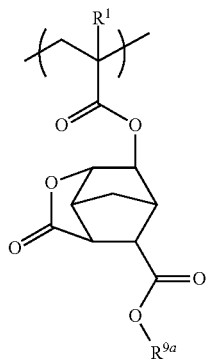

(10e) 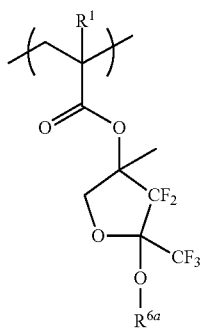

(10f) 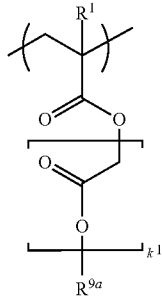

(10g) 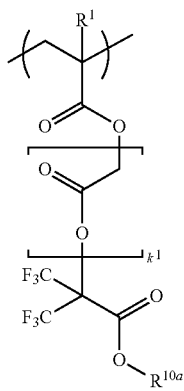

(10h) 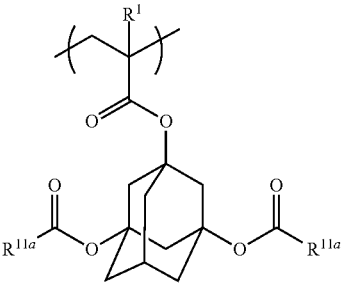

(10i) 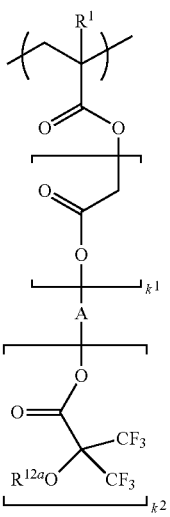

wherein $R^1$ is as defined above, $R^{5a}$ and $R^{5b}$ are hydrogen or a straight, branched or cyclic, $C_1$-$C_{15}$ monovalent hydrocarbon group, and $R^{5a}$ and $R^{5b}$ may bond together to form a $C_3$-$C_8$ non-aromatic ring with the carbon atom to which they are attached, $R^{6a}$ is hydrogen, a straight, branched or cyclic, $C_1$-$C_{15}$ monovalent hydrocarbon or fluorinated hydrocarbon group in which any constituent moiety —$CH_2$— may be replaced by —O— or —C(=O)—, or an acid labile group, $R^{7a}$, $R^{7b}$, and $R^{7c}$ are hydrogen, or a straight, branched or cyclic, $C_1$-$C_{15}$ monovalent hydrocarbon group, and a pair of $R^{7a}$ and $R^{7b}$, $R^{7a}$ and $R^{7c}$, and $R^{7b}$ and $R^{7c}$ may bond together to form a $C_3$-$C_8$ non-aromatic ring with the carbon atom to which they are attached, $R^{8a}$ is hydrogen or a straight, branched or cyclic, $C_1$-$C_{15}$ monovalent hydrocarbon group, $R^{8b}$ is a straight, branched or cyclic, $C_1$-$C_{15}$ monovalent hydrocarbon group, and $R^{8a}$ and $R^{8b}$ may bond together to form a $C_3$-$C_8$ non-aromatic ring with the carbon atom to which they are attached, $R^{9a}$ is a straight, branched or cyclic, $C_1$-$C_{15}$ monovalent fluorinated hydrocarbon group, $R^{10a}$ is a straight, branched or cyclic, $C_1$-$C_{15}$ monovalent hydrocarbon or fluorinated hydrocarbon group, $R^{11a}$ is a straight, branched or cyclic, $C_1$-$C_{10}$ monovalent fluorinated hydrocarbon group, $R^{12a}$ is hydrogen or a straight, branched or cyclic, $C_1$-$C_{20}$ monovalent hydrocarbon group in which any constituent moiety —$CH_2$— may be replaced by —O— or —C(=O)—, A is a straight, branched or cyclic, ($k^2$+1)-valent hydrocarbon or fluorinated hydrocarbon group of 1 to 20 carbon atoms, the subscript $k^1$ is 0 or 1, and $k^2$ is 1, 2 or 3.

4. A resist material comprising as a base resin a polymer comprising recurring units having lactone ring and/or hydroxyl group and/or recurring units having a structure derived from maleic anhydride, the polymer turning soluble in alkali developer under the action of acid, the polymer of claim 2 as an additive polymer, and an organic solvent.

* * * * *